(12) United States Patent
An et al.

(10) Patent No.: US 8,252,822 B2
(45) Date of Patent: Aug. 28, 2012

(54) HETEROCYCLIC COMPOUNDS AND USES AS ANTICANCER AGENTS

(75) Inventors: Haoyun An, Carlsbad, CA (US); Biao Xi, San Diego, CA (US); Yama Abassi, Temecula, CA (US); Xiaobo Wang, San Diego, CA (US); Xiao Xu, San Diego, CA (US)

(73) Assignee: Acea Biosciences, Inc., San Diego, CA (US)

( * ) Notice: Subject to any disclaimer, the term of this patent is extended or adjusted under 35 U.S.C. 154(b) by 672 days.

(21) Appl. No.: 12/175,154

(22) Filed: Jul. 17, 2008

(65) Prior Publication Data

US 2009/0048271 A1    Feb. 19, 2009

Related U.S. Application Data

(60) Provisional application No. 60/950,191, filed on Jul. 17, 2007, provisional application No. 60/950,197, filed on Jul. 17, 2007.

(51) Int. Cl.
*A61K 31/429*    (2006.01)
*C07D 513/04*    (2006.01)

(52) U.S. Cl. ........................................ 514/368; 548/154
(58) Field of Classification Search .................. 514/368; 548/154
See application file for complete search history.

(56) References Cited

U.S. PATENT DOCUMENTS

| | | | |
|---|---|---|---|
| 4,810,643 A | 3/1989 | Souza | |
| 4,999,291 A | 3/1991 | Souza | |
| 5,229,496 A | 7/1993 | Deeley et al. | |
| 5,391,485 A | 2/1995 | Deeley et al. | |
| 5,393,870 A | 2/1995 | Deeley et al. | |
| 5,580,755 A | 12/1996 | Souza | |
| 5,582,823 A | 12/1996 | Souza | |
| 7,167,585 B2 | 1/2007 | Gounares et al. | |
| 7,459,303 B2 | 12/2008 | Wang et al. | |
| 7,468,255 B2 | 12/2008 | Xu et al. | |
| 7,470,533 B2 | 12/2008 | Xu et al. | |
| 2004/0152067 A1 | 8/2004 | Wang et al. | |
| 2005/0112544 A1 | 5/2005 | Xu et al. | |
| 2005/0227989 A1 | 10/2005 | Wang et al. | |

FOREIGN PATENT DOCUMENTS

| | | | |
|---|---|---|---|
| JP | 2003-313176 | 11/2003 | |
| JP | 2003313176 A | * 11/2003 | |
| WO | WO-01/64674 | 9/2001 | |
| WO | WO-03/015773 | 2/2003 | |
| WO | WO-2004/010102 | 1/2004 | |
| WO | WO-2004/010103 | 1/2004 | |
| WO | WO-2006/122011 | 11/2006 | |
| WO | WO 2006122011 A2 | * 11/2006 | |
| WO | WO-2007/031440 | 3/2007 | |
| WO | WO-2009/023402 | 2/2009 | |
| WO | WO-2010/002985 | 1/2010 | |

OTHER PUBLICATIONS

Registry Entry 620602-36-0, entered Nov. 25, 2003.*
International Search Report and Written Opinion for PCT/US08/70348, mailed Feb. 24, 2009, 9 pages.
Andreani et al., Arkivoc (2004) v:76-84.
Andreani et al., Biorg. Med. Chem. (2000) 8:2359-2366.
Andreani et al., Biorg. Med. Chem. (2004) 12:5525-5532.
Andreani et al., Collect. Czech. Chem. Commun. (2000) 65:267-279.
Andreani et al., J. Med. Chem. (2006) 49:7897-7901.
Bowman et al., Arkivoc (2003) x:434-442.
Carballares et al., Tetrahedron Lett. (2007) 48:2041-2045.
Ermolat'Ev et al., J. Comb. Chem. (2006) 8:659-663.
Farb et al., Circulation (1999) 99:44-52.
Hayakawa et al., Biorg. Med. Chem. (2007) 15:403-412.
Morice et al., New Engl J Med (2002) 346:1773-1780.
Moses et al., New Engl J Med (2003) 349:1315-1323.
Nafziger et al., Cytotechnology (1991) 6:227-232.
Nakagawa et al., Biorg. Med. Chem. (2000) 8:2663-2673.
Panda et al., PNAS USA (1997) 94:10560-10564.
Rupert et al., Biorg. Med. Chem. Lett. (2003) 13:347-350.
Saldabol et al., Engl. Transl. of Khimiya Geterotsiklichecskikh Soedinenii (1975) 1:55-61.
Stone et al., New Engl J Med (2004) 350:221-231.
U.S. Appl. No. 60/379,749, filed Jul. 20, 2002.
U.S. Appl. No. 60/435,400, filed Dec. 20, 2002.
U.S. Appl. No. 60/469,572, filed May 9, 2003.
U.S. Appl. No. 60/519,567, filed Nov. 12, 2003.
U.S. Appl. No. 60/542,927, filed Feb. 9, 2004.
Witte et al., Cancer Metastasis Rev. (1998) 17:155-161.
Yeung et al., Biochim. Biophys. Res. Comm. (1997) 263:398-404.
Supplementary European Search Report for EP 08827232.3, mailed Nov. 10, 2010, 9 pages.
Berge et al., J. Pharm. Sci. (1977) 66:1-19.
Emens et al., Curr. Opinion Mol. Ther. (2001) 3(1):77-84.
Leone et al., Bioorganic & Medicinal Chemistry (2008) 16(10):5695-5703.
Penichet and Morrison, J. Immunol. Methods (2001) 248:91-101.
International Search Report and Written Opinion for PCT/US2011/025550, mailed on May 26, 2011, 13 pages.

* cited by examiner

*Primary Examiner* — Joseph Kosack
(74) *Attorney, Agent, or Firm* — Morrison and Foerster LLP

(57) ABSTRACT

Novel compounds having a fused bicyclic heteroaromatic ring system substituted with a heteroaryl five-membered ring are disclosed. The compounds inhibit growth of a variety of types of cancer cells, and are thus useful for treating cancer. Efficacy of these compounds is demonstrated with a system for monitoring cell growth/migration, which shows they are potent inhibitors of growth and/or migration of cancer cells. In addition, compounds of the invention were shown to stop growth of tumors in vivo, and to reduce the size of tumors in vivo. Compositions comprising these compounds, and methods to use these compounds and compositions for treatment of cancers, are disclosed.

9 Claims, 17 Drawing Sheets

HETEROCYCLIC COMPOUNDS AND USES AS ANTICANCER AGENTS

RELATED APPLICATIONS

This application claims priority to U.S. Provisional Patent Application No. 60/950,191, filed Jul. 17, 2007, and to U.S. Provisional Patent Application No. 60/950,197, filed Jul. 17, 2007, and the contents of each of these applications are incorporated herein by reference in their entirety.

FIELD OF THE INVENTION

The field of the invention is heterocyclic compounds, pharmaceutical compositions and methods, and especially as they relate to compositions and methods for the treatment and prevention of cancer and related diseases.

BACKGROUND OF THE INVENTION

Cancer, including over 200 diseases, is the second biggest cause of death in the developed countries. Therefore, cancer remains one of the most important unmet medical challenges to mankind. A number of options for treating tumors are available, including surgery, radiation, chemotherapy, or any combination of these approaches. Among these, chemotherapy is widely used for all types of cancers, in particular for those inoperable or with metastatic characteristics. Despite a variety of chemotherapeutic compounds being used in clinics for improvement of survival rates of different human cancers, chemotherapy is generally not curative, but only delays disease progression. Commonly, tumors and their metastasis become refractory to chemotherapy, as the tumor cells develop the ability of multi-drug resistance. In some cases, the tumors are inherently resistant to some classes of chemotherapeutic agents. In other cases, the acquired resistance against chemotherapeutic agents is developed during the chemotherapeutic intervention. Thus, there remain significant limitations to the efficacy of available chemotherapeutic compounds in treating different classes of tumors. Furthermore, many cytotoxic and cytostatic agents used for chemotherapeutic treatment of tumors have severe side effects, resulting in termination of the chemotherapy in some patients. Thus, there remains a need for new chemotherapeutic agents.

BRIEF SUMMARY OF INVENTIONS

The present invention is directed to various classes of heteroaryl-substituted bicyclic heteroaryl derivatives, pharmaceutical compositions, and methods of using thereof. Exemplary embodiments have a thiazole or oxazole or imidazole heterocyclic moiety that is further substituted with an optionally substituted aryl amino, arylthio, aryloxy, heterocyclic amino, heterocyclic thio, or heterocyclic oxy group. The compounds as described herein exhibit anti-tumor, anticancer, anti-inflammation, anti-infectious, and antiproliferation activity. The present invention also relates to the methods of making and formulating the described compounds. The present invention also relates to pharmaceutical compositions containing such compounds that may be used for treating tumors, cancer, infective and/or proliferative diseases.

In one aspect of the inventive subject matter, contemplated heterocyclic compounds will generally have a structure according to Formula I and II:

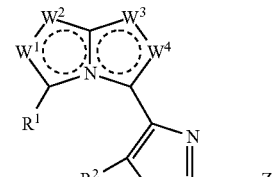

Formula I

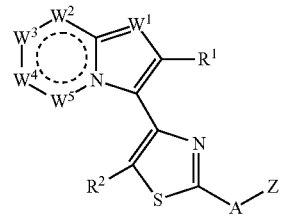

Formula II where ◯ in a ring indicates the ring is an aromatic or heteroaromatic ring;
each $W^1$, $W^2$, $W^3$, and $W^4$ is independently N, S, O, or $CR^3$;
$W^5$ is S or O or $CR^3$;
A is NH, $NR^4$, S, SO, $SO_2$, O, Se, B (Boron), $NHSO_2$, $NR^4SO_2$, $SO_2NH$, $SO_2NR^4$, OP(=O)($OR^4$), $NR^4C(O)$, $C(O)NR^4$;
and Z is Ar, any fused-heterocyclic group, or $CH_2Ar$, where Ar is a 5-10 atom monocyclic or bicyclic aromatic group that is optionally substituted with up to five substituents, and may contain up to four heteroatoms selected from N, O and S as ring members;
each of $R^1$, $R^2$, $R^3$, and $R^4$ is H, OH, NHR, NRR', OR, SR, substituted or unsubstituted alkyl, alkenyl, alkynyl, aryl, fused aryl, heteroaryl, fused heterocycle, a carbocyclic ring or a heterocyclic ring, each of which is optionally substituted and may contain a heteroatom selected from N, O and S in place of one carbon atom,
and two $R^1$, $R^2$, $R^3$, or $R^4$ on the same or adjacent atoms can optionally be linked together to form a 3-8 membered ring that can contain up to two heteroatoms selected from N, O and S as ring members and which is optionally substituted;
where each R and R' is H, alkyl, alkenyl, alkynyl, aryl, or heteroaryl, wherein each alkyl, alkenyl, alkynyl, aryl and heteroaryl is optionally substituted,
and where R and R' if present on the same or adjacent atoms can optionally cyclize to form a 3-8 membered ring containing up to two heteroatoms selected from N, O and S;
or a pharmaceutically acceptable salt or metabolite thereof.

In formula (I) compounds, Z is sometimes substituted with up to three substituents.
In compounds of formula (II), preferably not more than one of $W^2$, $W^3$, $W^4$ and $W^5$ is a bond, and at least one of $W^2$, $W^3$, $W^4$ and $W^5$ is not $CR^3$; and not more than two of $W^2$, $W^3$, $W^4$ and $W^5$ represent N, but at least one of $W^2$, $W^3$, $W^4$ and $W^5$ is $CR^3$. In these compounds, it is sometimes preferred that Z is not unsubstituted imidazopyridine, and when A is NAc, Z is not methoxy-substituted pyridinyl. In some embodiments, if $W^1$ is N, $R^1$ is Me and A is NH, then Z is not —$CH_2$-(2-furanyl), unsubstituted phenyl, unsubstituted benzyl, or phenyl substituted with —$NO_2$, Br, —OH, —NHAc, $SO_2NH$-heteroaryl, or COOH. In the compounds of formula (II), when Z is S, SO or $SO_2$, $R^1$ is preferably not H when $W^2$ is CH.

In some embodiments, the invention provides compounds having formula III, IV, V, VI or VII:

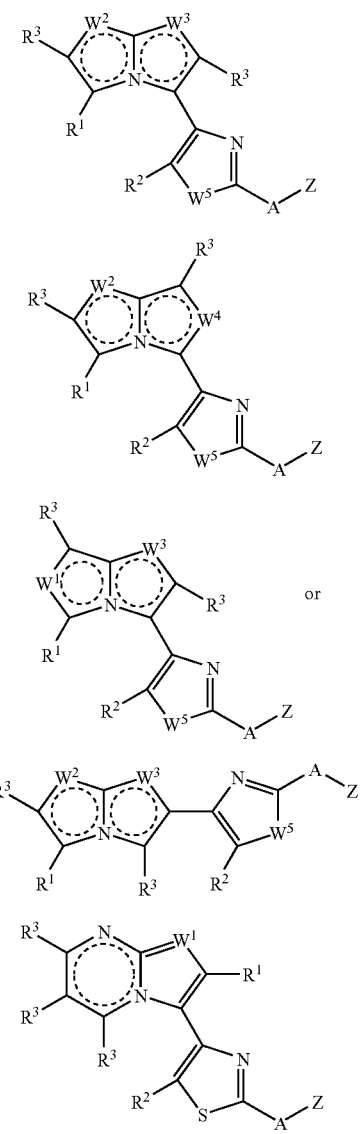

where $W^1$, $W^2$, $W^3$, $W^4$, $W^5$, Z, A and $R^1$, $R^2$, $R^3$, and $R^4$ are as defined above.

In the above formula I-VII, Z may be an aromatic or heterocyclic moiety selected from the following structures:

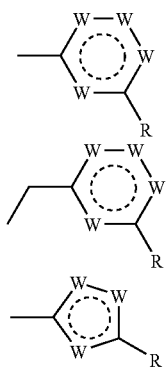

wherein is as defined above;
each W is independently CR', N, NR', S, or O; and
each R' is as defined above;
and R is selected from H, halo, OR', SR', $CO_2R'$, $C(O)NR'_2$, C=O, CN, $CF_3$, $OCF_3$, $NO_2$, NR'R', OCOR', $NR'SO_2R'$, $SO_2NR'R'$, $SO_3R'$, $P(O_3R')$, $CH(COOR')_2$, $CH(PO_3R')_2$, where R' is as defined above, or R is $C_{1-8}$ alkyl, $C_{3-8}$ cyclic alkyl, $C_{2-8}$ alkenyl, $C_{2-8}$ alkynyl, an aryl, heteroaryl, a carbocyclic ring or a heterocyclic ring, each of which may contain a heteroatom.

The aromatic ring(s) comprising Z can be substituted by up to five groups other than H, preferably up to four such groups, and in some embodiments with up to three groups other than H. Preferably, Z is substituted with 1-3 non-hydrogen groups. These groups can be at any position of the aryl/heteroaryl ring of Z. When Z is a 6-membered ring, in some embodiments at least one substituent other than H is present at the para position of the ring, or at the meta position of the ring.

In some embodiments, Z is selected from:

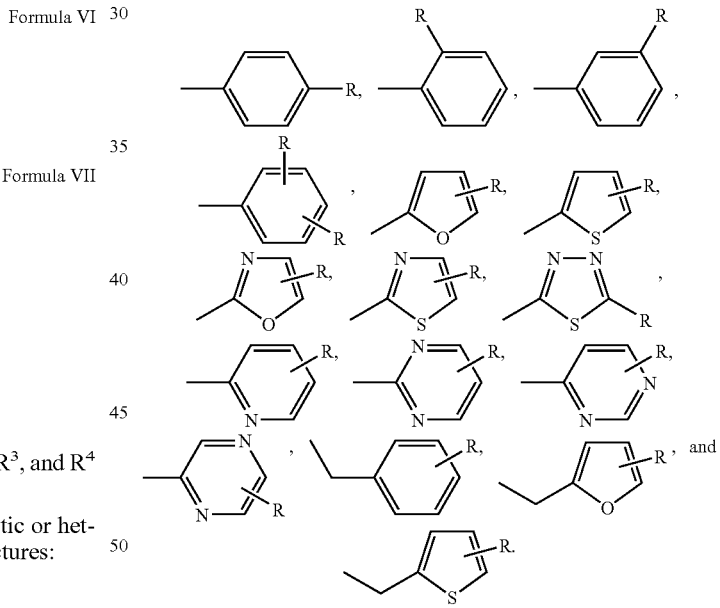

where each R group is as defined above. Some preferred groups that R can represent are listed in Table 1. Specific embodiments of the portion of these compounds of formula I-VII corresponding to -A-Z are set forth in Tables 3-7, and are preferred embodiments of -A-Z in each class of compounds related to the invention.

In some embodiments of the compounds of formula (II-VII), when $W^2$ is S and $W^3$ is N and $W^4$ is CMe, Z is preferably not a benzyl group; a phenyl substituted with more than one Br or with $SO_2NRR$; $CH_2$-(2-furanyl); or methoxy-substituted pyridyl. In other embodiments, however, such as for methods of treating cancer, these limitations may not be applicable.

In the above formula I-VII, Z may be mono-/di-/tri-substituted or unsubstituted benzene, pyridine, pyridazine, pyrimidine, pyrazine, triazine, oxazole, isoxazole, thiazole, isothiazole, oxadiazole, triazole, thiadiazole, pyrazole, imidazole, benzoxazole, pyrrole, furan, thiophene, indolizine, indole, isoindole, indoline, benzofuran, benzothiophene, indazole, benzimidazole, benzthiazole, purine, quinoxaline, quinoline, isoquinoline, cinnoline, phthalazine, quinazoline, naphthyridine, pteridine, acridine, phenazine, phenothiazine, indene, naphthalene, benzoxadiazole or any fused-heterocyclic moieties. When Z is the aromatic or heterocylic systems described herein, it is sometimes substituted with halo, OR, SR, O((CH2)pO)qR, CO2R, C(O)NR2, C(=O)R, CN, CF3, OCF3, NO2, NRR, OCOR, SO3H, NRSO2R, or SO2NRR, where each p is independently is 1-4 and q is 1-6. Other suitable substituents include C1-8 alkyl, C2-8 alkenyl, C2-8 alkynyl, C3-8 cyclic alkyl, C2-8 alkenyl, C2-8 alkynyl, an aryl, heteroaryl, a carbocyclic ring or a heterocyclic ring, each of which can also be substituted. In these substituents, each R is C1-8 alkyl that is optionally substituted with one or more halo, =O, =N—CN, =N—OR', =NR', OR', NR'2, SR', SO2R', SO2NR'2, NR'SO2R', NR'CONR'2, NR'COOR', NR'COR', CN, COOR', CONR'2, OOCR', COR', and NO2, wherein each R' is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R' is optionally substituted with halo, =O, =N—CN, =N—OR", =NR", OR", NR"2, SR", SO2R", SO2NR"2, NR"SO2R", NR"CONR"2, NR"COOR", NR"COR", CN, COOR", CONR"2, OOCR", COR", and NO2, wherein each R" is independently H, C1-C8 alkyl, C2-C8 heteroalkyl, C1-C8 acyl, C2-C8 heteroacyl, C6-C10 aryl or C5-C10 heteroaryl; and when two R' or R" are present on one atom or on adjacent atoms, they can be linked together to form a 3-8 membered ring that is optionally substituted and may contain up to two heteroatoms selected from N, O and S as ring members. Each alkyl, alkenyl and alkynyl described can be substituted with one or more F. In some embodiments of Formula I or III, $W^2$ is S and $W^3$ is N.

In some of the foregoing compounds, $W^5$ is S.

In some of the foregoing compounds, A is $NR^4$, where $R^4$ is as defined above. In some such embodiments, $R^4$ is an acyl group, e.g. —C(=O)—(C1-8 alkyl) or $R^4$ is H. In some preferred embodiments, $R^4$ is H.

In some embodiments of the foregoing compounds, Z is Ar, where Ar represents substituted or unsubstituted phenyl. In some embodiments, Z is —CH2—Ar, where Ar is substituted or unsubstituted phenyl. In preferred embodiments, Ar is substituted with at least one group such as halo, C1-C4 alkoxy, OH, C1-C4 alkyl, or C1-C4 alkyl substituted with =O, or with one or more F, Cl, CN, $CF_3$, Br, NRR', COOR', and/or CONRR', where R is C1-C4 alkyl that is optionally substituted with one or more F, Cl, CN, $CF_3$, Br or C1-C4 alkoxy; and when two R are present on one atom or on adjacent atoms, they can be linked together to form a 3-8 membered ring that is optionally substituted and may contain up to two heteroatoms selected from N, O and S as ring members. Where two substituents on Ar are on adjacent atoms, they can optionally cyclize to form a 5-8 membered ring that can be substituted and can contain up to two heteroatoms selected from N, O and S as ring members.

In certain embodiments, the invention provides compounds of formula IIIa or VIIa:

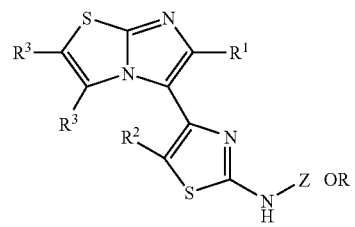

IIIa

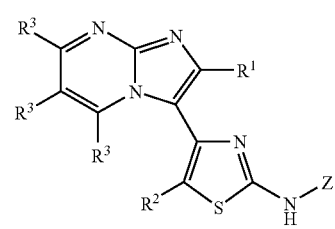

VIIa wherein $R^1$ is optionally substituted C1-C4 alkyl;

each $R^3$ is independently H, halo, C1-C4 alkoxy, or C1-C4 alkyl;

$R^2$ is H, halo, C1-C4 alkoxy, or C1-C4 alkyl;

wherein Z is selected from the group consisting of:

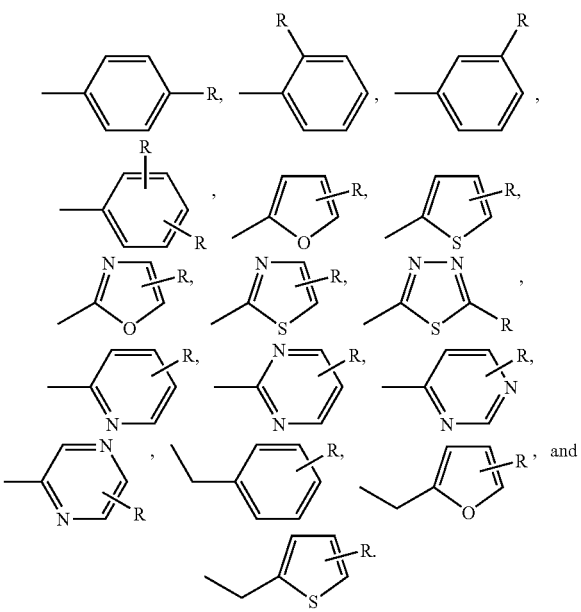

or a pharmaceutically acceptable salt thereof.

Some embodiments of these compounds have formula VIII or IX:

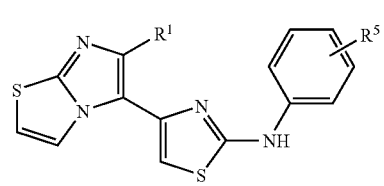

Formula VIII

Formula IX

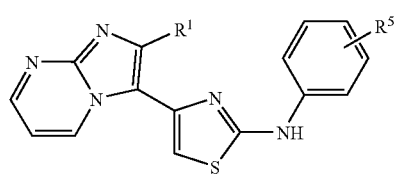

wherein each $R^1$ is as defined above;

And $R^5$ is OR', SR', NR'$_2$, OCHF$_2$, OCF$_3$, CF$_3$, OCH$_2$CF$_3$, OCF$_2$CF$_3$, F, halo, (CF$_2$)$_{2-7}$CF$_3$, O(CH$_2$CH$_2$)R', O(CH$_2$CH$_2$O)$_{0-6}$H, O(CH$_2$CH$_2$)$_{1-2}$R', And $R^5$ can also be selected from the following groups:

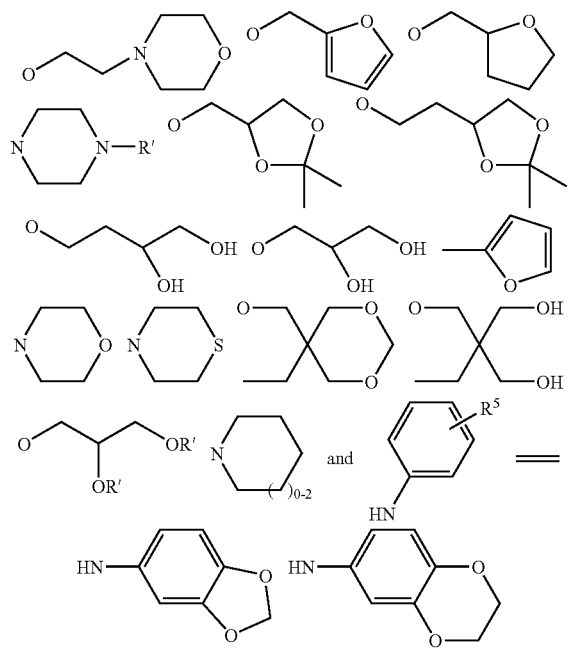

where R' is as defined above;
and 1-5 such $R^5$ groups can be attached on the same benzene ring.

In some such embodiments, the group corresponding to —NH-Z in formula IIIa or VIIa is selected from the group consisting of:

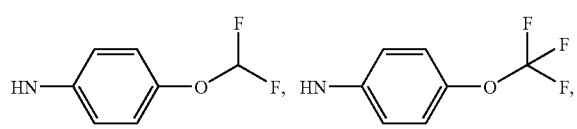

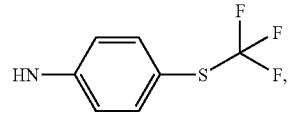

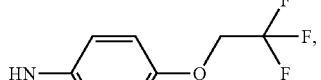

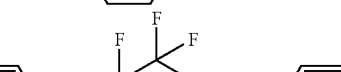

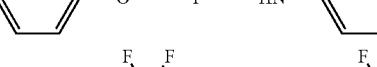

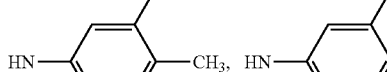

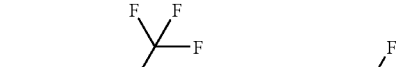

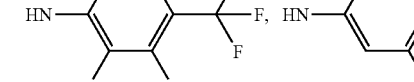

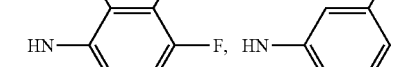

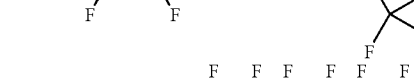

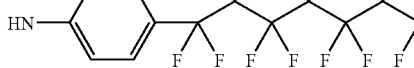

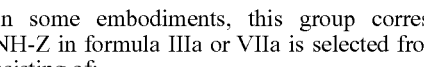

In some embodiments, this group corresponding to —NH-Z in formula IIIa or VIIa is selected from the group consisting of:

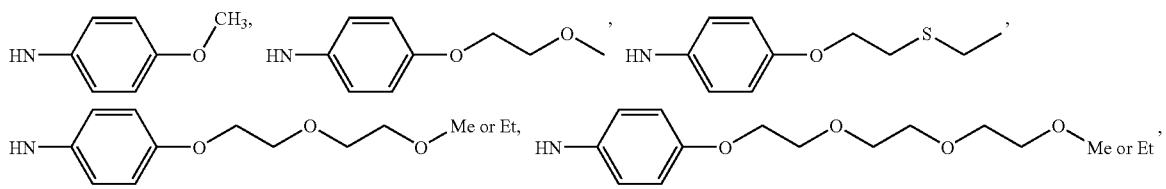

-continued

[Chemical structures showing various HN-phenyl compounds with different oxyethylene/hydroxyl substituents]

In some of these compounds, $R^1$ is Methyl.
In some of these compounds $R^2$ is H.
In some of these compounds, $R^3$ is H.

In another aspect, the invention provides compounds of formula (VI) as set forth above, and compositions comprising such compounds, and methods of using such compounds for treating various conditions described herein, including cancers.

In some embodiments of the compounds of formula (VI), $W^5$ is S.

In some embodiments of the compounds of formula (VI), $W^2$ is S.

In some embodiments of the compounds of formula (VI), $W^3$ is N.

In another aspect, the invention provides compounds, compositions and uses thereof wherein the compounds have the following structure:

Formula (X)

[Chemical structure of Formula (X)]

where ◯ in a ring indicates that the ring is an aromatic or heteroaromatic ring;

$W^1$ is $CR^3$ or N;

each of $W^2$, $W^3$, and $W^5$ is $CR^3$, N, O, or S or a bond,
provided not more than one of $W^2$, $W^3$, $W^4$ and $W^5$ is a bond, and at least one of $W^2$, $W^3$, $W^4$ and $W^5$ is not $CR^3$;

and not more than two of $W^2$, $W^3$, $W^4$ and $W^5$ represent N;

and at least one of $W^2$, $W^3$ and $W^5$ is $CR^3$;

A is NH, $NR^5$, S, SO, $SO_2$, O, Se, B (Boron), $NHSO_2$, $NR^5SO_2$, $SO_2NH$, $SO_2NR^5$, $OP(=O)OR^5$, NHC(O), or C(O)NH;

Z is Ar or $CH_2Ar$, where Ar is a 5-10 atom monocyclic or bicyclic aromatic group containing 0-4 heteroatoms selected from N, O and S as ring members and optionally substituted with up to four $R^4$;

provided Z is not unsubstituted imidazopyridine, and when A is NAc, Z is not methoxy-substituted pyridinyl;

each of $R^1$, $R^2$, $R^3$, $R^4$, $R^5$ is independently H, halo, OR, NRR', $S(O)_mR$, COOR, $SO_2NRR'$, $NO_2$, CN, or a substituted or unsubstituted alkyl, alkenyl, alkynyl, aryl, fused aryl, heteroaryl, fused heterocycle, carbocyclic ring or heterocyclic ring, and two $R^1$, $R^2$, $R^3$, $R^4$, $R^5$ on the same or adjacent atoms can optionally be linked together to form a 3-8 membered ring that can contain up to two heteroatoms selected from N, O and S as ring members and which is optionally substituted;

where each R and R' is H, alkyl, alkenyl, alkynyl, aryl, or heteroaryl, wherein each alkyl, alkenyl, alkynyl, aryl and heteroaryl is optionally substituted, and where R and R' if present on the same or adjacent atoms can optionally cyclize to form a 3-8 membered ring containing up to two heteroatoms selected from N, O and S;

m is 0-2; and and pharmaceutically acceptable salts thereof.

Particular embodiments of these compounds have the formula:

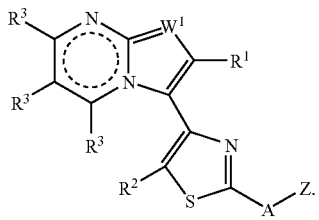

Formula VII

For these compounds, in certain embodiments, Z is not unsubstituted imidazopyridine, and when A is NAc, Z is not methoxy-substituted pyridinyl; and when $W^1$ is N, $R^1$ is Me and A is NH, Z is not —$CH_2$-(2-furanyl), unsubstituted phenyl, unsubstituted benzyl, or phenyl substituted with —$NO_2$, Br, —OH, —NHAc, $SO_2$NH-heteroaryl, or COOH. Preferably, A and Z are as described above, so exemplary embodiments of Z are described in Tables 3-7, and A is sometimes NH.

In some embodiments of Formula X or VII, Z is selected from structures depicted in Tables 1-2. In some embodiments, Z is substituted with one or more, typically up to three groups selected from halo, OR, SR, $CO_2$R, C(O)$NR_2$, C(=O)R, CN, $CF_3$, $OCF_3$, $NO_2$, NRR', OCOR, $SO_3$H, $NRSO_2$R, $SO_2$NRR'; or R is $C_{1-8}$ alkyl, $C_{3-8}$ cyclic alkyl, $C_{2-8}$ alkenyl, $C_{2-8}$ alkynyl, an aryl, heteroaryl, a carbocyclic ring or a heterocyclic ring, each of which may contain a heteroatom;
  where each R and R' is H, alkyl, alkenyl, alkynyl, aryl, or heteroaryl, wherein each alkyl, alkenyl, alkynyl, aryl and heteroaryl is optionally substituted,
  and where R and R' if present on the same or adjacent atoms can optionally cyclize to form a 3-8 membered ring containing up to two heteroatoms selected from N, O and S.

In some embodiments, Z is substituted with at least one such group.

In some of these compounds, $W^1$ is N or CH. Frequently, $W^1$ is N.

In some of these compounds, $R^1$ is H, halo or optionally substituted C1-C4 alkyl.

In some of the foregoing embodiments, each $R^3$ is selected from H, halo, CN, optionally substituted C1-C4 alkyl, and C1-C4 alkoxy.

In some of the foregoing embodiments, $R^2$ is H, halo, CN, CONRR', COOR', or $CF_3$, or an optionally substituted C1-C4 alkyl or alkoxy.

In some of the foregoing embodiments, wherein A is $NR^5$ or O or S, where $R^5$ is as defined above.

In some of the foregoing embodiments, A is NH or $NR^5$, where $R^5$ is optionally substituted C1-C4 alkyl or a C1-C4 acyl group.

In some of the foregoing embodiments, Z is a 5-membered aromatic or heteroaromatic ring or a 6-membered aromatic or heteroaromatic ring that is substituted with 0-3 substituents.

In some of the foregoing embodiments, Z is a substituted phenyl ring or a substituted or unsubstituted 2-pyridyl, 3-pyridyl or 4-pyridyl ring. Phenyl is sometimes preferred.

The compounds in above formula I-X can be used as neutral compounds or as their pharmaceutically suitable salts with inorganic and organic anions. Their salts include, but are not limited to, halides (Cl⁻, Br⁻, I⁻), nitrate, mesylate, p-toluene sulfonate/tosulate, oxalate, citrate, malate, maleate, tartrate, fumarate, formate, acetate and the similar anions in the classes.

The above-described heterocyclic compounds include the compounds themselves, as well as their salts and their prodrugs, if applicable. Such salts, for example, can be formed between a positively charged substitute group (e.g., an amino group on heterocyclic or aromatic rings) on a compound and a pharmaceutically suitable anion. Suitable anions include, but are not limited to, chloride, bromide, iodide, sulfate, nitrate, phosphate, citrate, methanesulfonate, trifluoroacetate, maleate, and acetate. Similarly, a negatively charged substituted group (e.g., carboxylate group on heterocyclic or aromatic rings) on a compound can form a salt with a cation. Non-limiting examples of suitable cations are sodium ion, potassium ion, magnesium ion, calcium ion, and a organic ammonium ion such as teteramethylammonium ion, tetrabutylammonium ion, and other organic cations.

Compounds of the invention may exist as isomers, including optical isomers, geometric isomers, tautomers, and rotational isomers. The invention includes each such isomer of the compounds of formula I-X, and mixtures thereof. Where a compound has a chiral center, for example, the invention includes each individual isomer as well as mixtures of both isomers in varying amounts, including a racemic mixture having equal amounts of both isomers. Because the compounds of the invention are biaryls, they can exist as rotational isomers about the biaryl linkage, also, and each isomer as well as mixtures of such isomers are included within the scope of the invention.

The compounds and compositions comprising the compounds of the invention are useful to treat conditions characterized by undesired cell proliferation. In particular, the compounds are useful to treat sarcoma, epidermoid cancer, fibrosarcoma, cervical cancer, leukemia, lymphoma, lung cancer, non-small cell lung cancer, colon cancer, CNS cancer, melanoma, ovarian cancer, renal cancer, prostate cancer, breast cancer, head and neck cancers, pancreatic cancer, and other types of a proliferative disease.

thiazole, ACEA100160) in Table 8 as determined on Real-Time Cell Electronic Sensing System.

Figure 6:
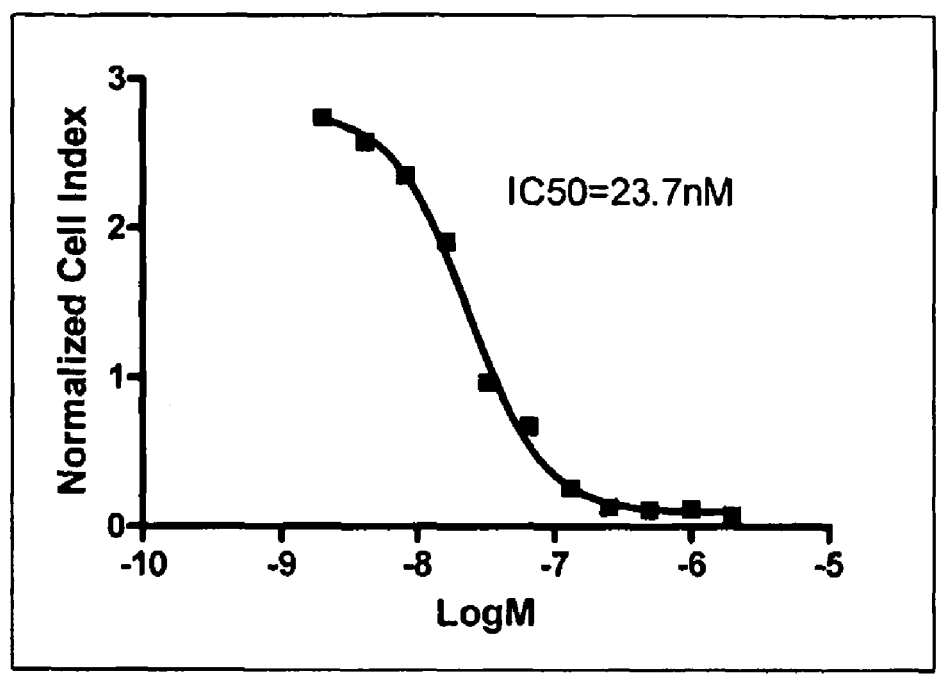

FIG. 6 shows dose response curves of A549 cells to the treatment of the compound No. 26 (2-(4-ethoxyphenyl)amino-4-(6-methylimidazo[1,2-a]pyrimidin-3-yl)thiazole, ACEA100160) in Table 8, at the treatment time of 24 hrs after treatment.

Figure 7:
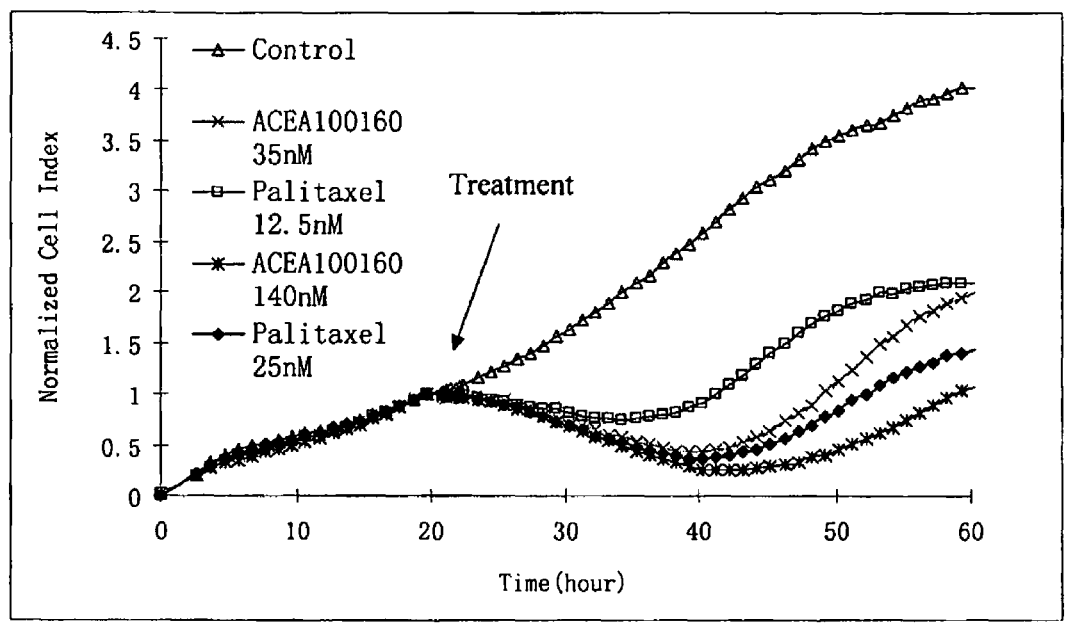

FIG. 7 shows the dynamic response pattern of A549 cell to different concentrations of paclitaxel and compound No. 26 (2-(4-ethoxyphenyl)amino-4-(6-methylimidazo[1,2-a]pyrimidin-3-yl)thiazole, ACEA100160) in Table 8, as determined on Real-Time Electronic Sensing System. Evidently, one can note that A549 cell exhibited similar responsive patterns to ACEA100160 in Table 8 and to paclitaxel.

Figure 8:
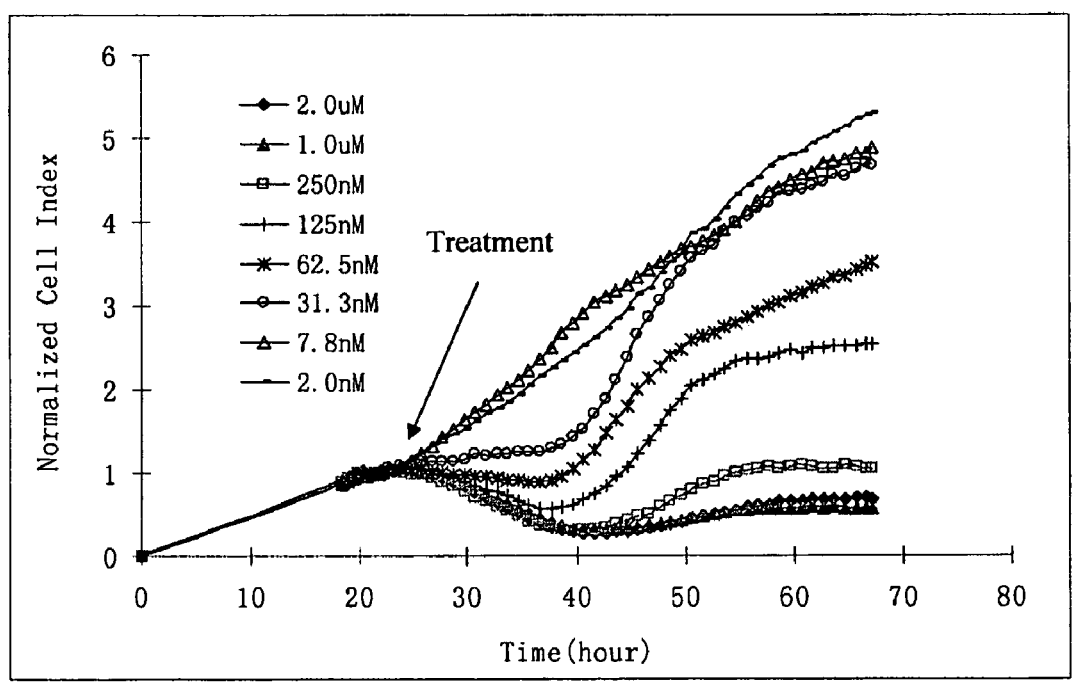

FIG. 8 shows the dynamic response pattern of A549 cells to different concentrations of compound No. 27 (2-(4-ethoxyphenyl)amino-4-(6-methylimidazo[2,1-b]thiazol-5-yl)thiazole, ACEA100162) in Table 8, as determined on Real-Time Cell Electronic Sensing System.

Figure 9:
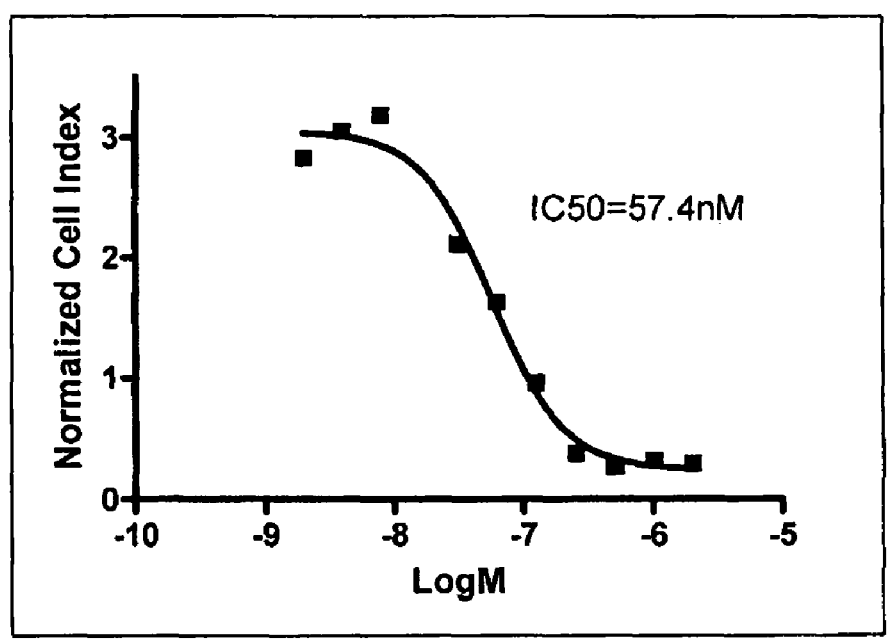

FIG. 9 shows dose response curves of A549 cells to the treatment of the compound No. 27 (2-(4-ethoxyphenyl)amino-4-(6-methylimidazo[2,1-b]thiazol-5-yl)thiazole, ACEA100162) in Table 8 at the treatment time of 24 hrs after treatment.

Figure 10:
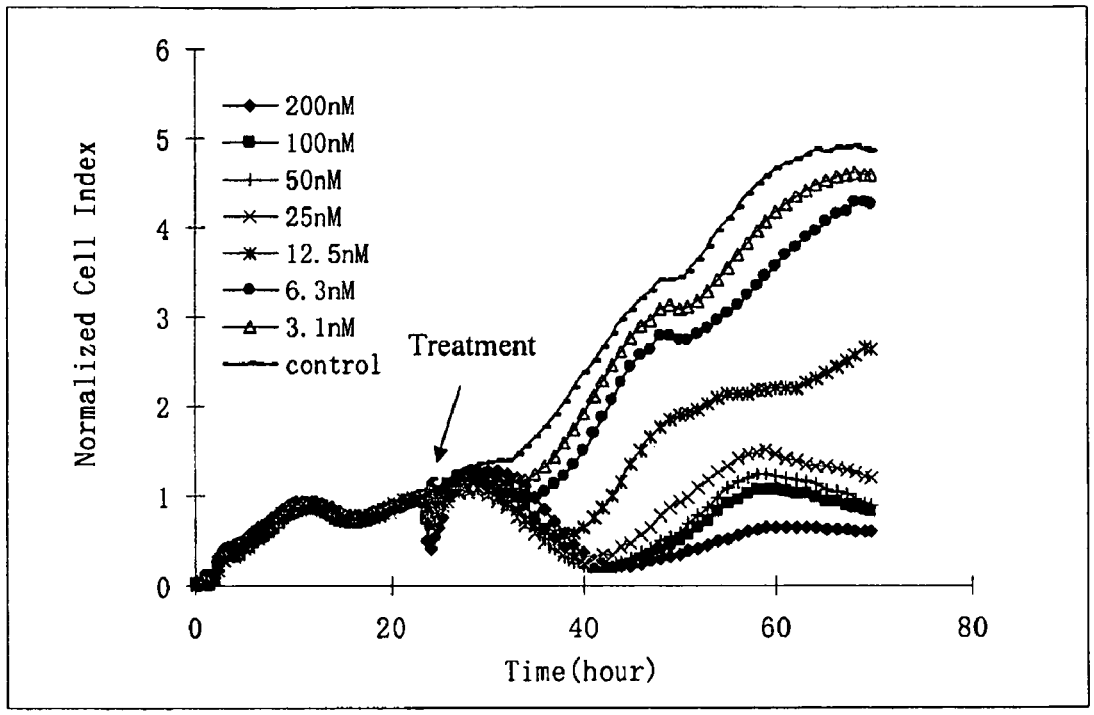
Figure 10:
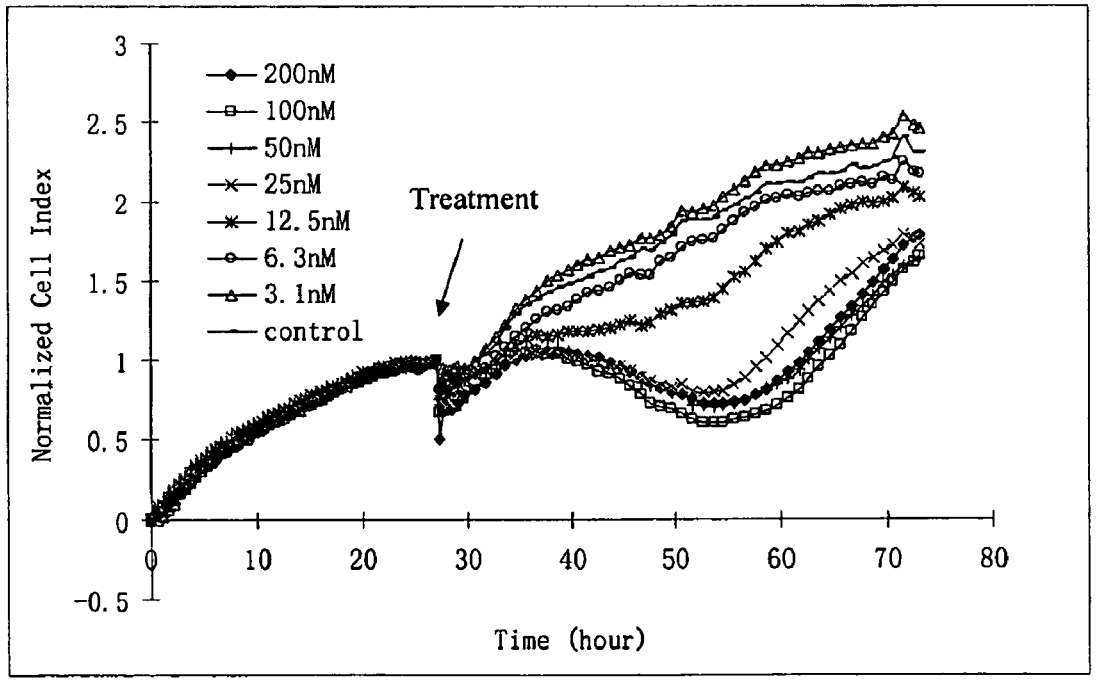
Figure 10:
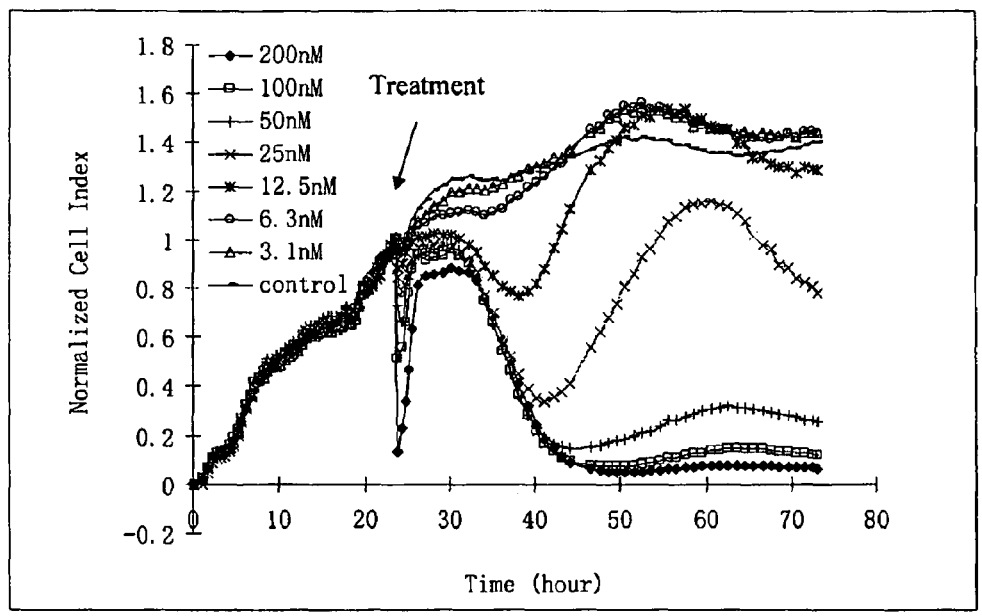
Figure 10:
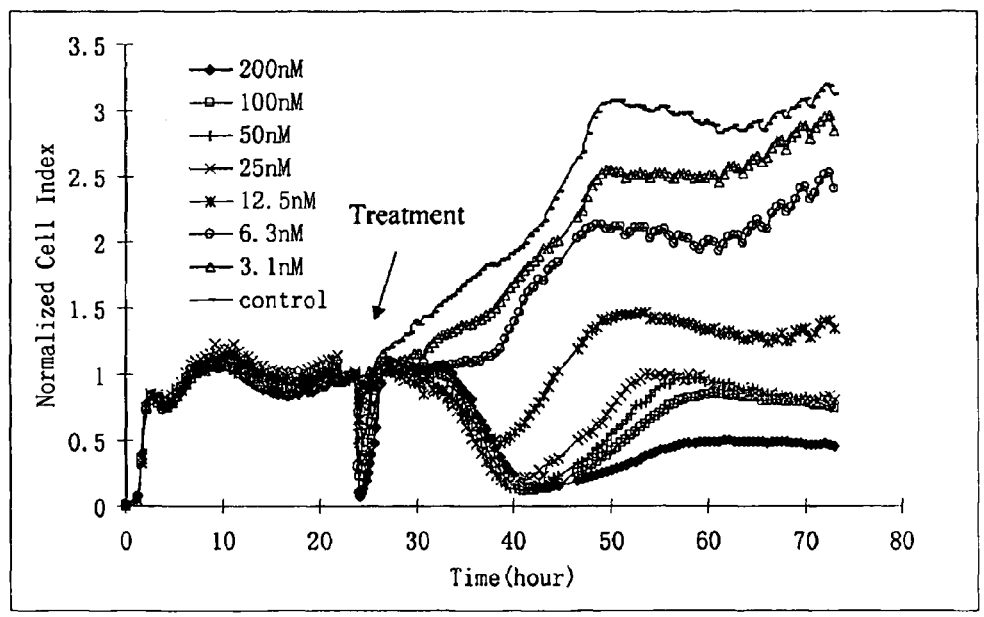
Figure 10E:
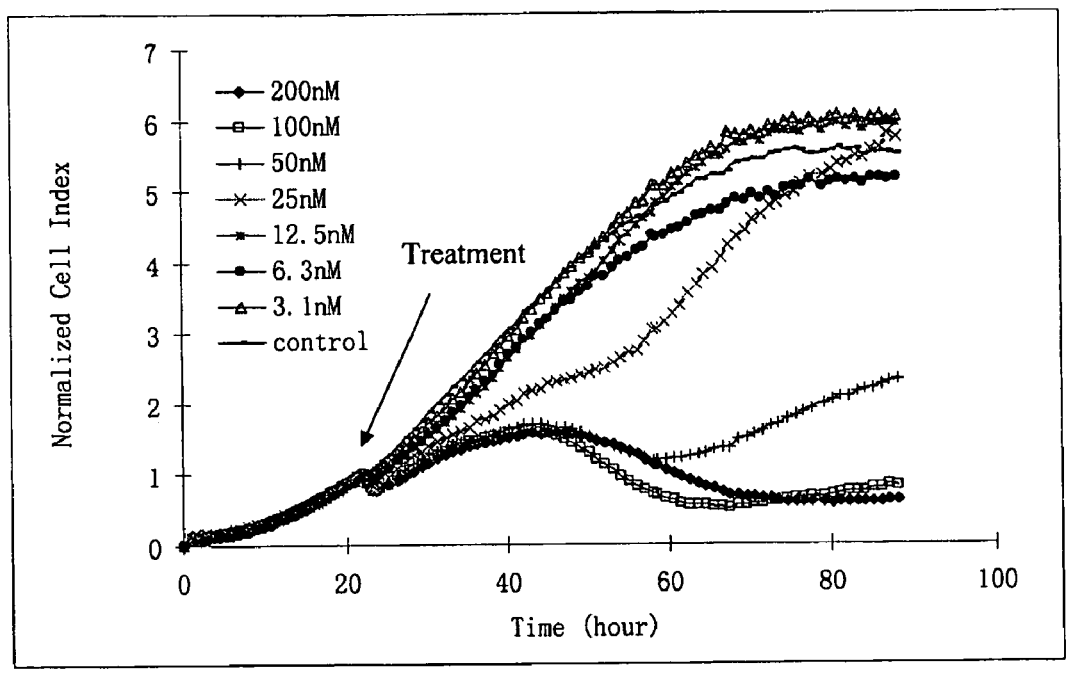

FIG. 10 shows the time-dependent cell index for a number of cell lines prior to and after addition of ACEA100162 at various concentrations: (A) MCF7adr (human breast adenocarcinoma), (B) PC3 (human prostate cancer), (C) KB (human head-neck cancer), (D) KB200 (human oral epithelioma) and (E) Bcap37 (human breast adenocarcinoma).

Figure 11:
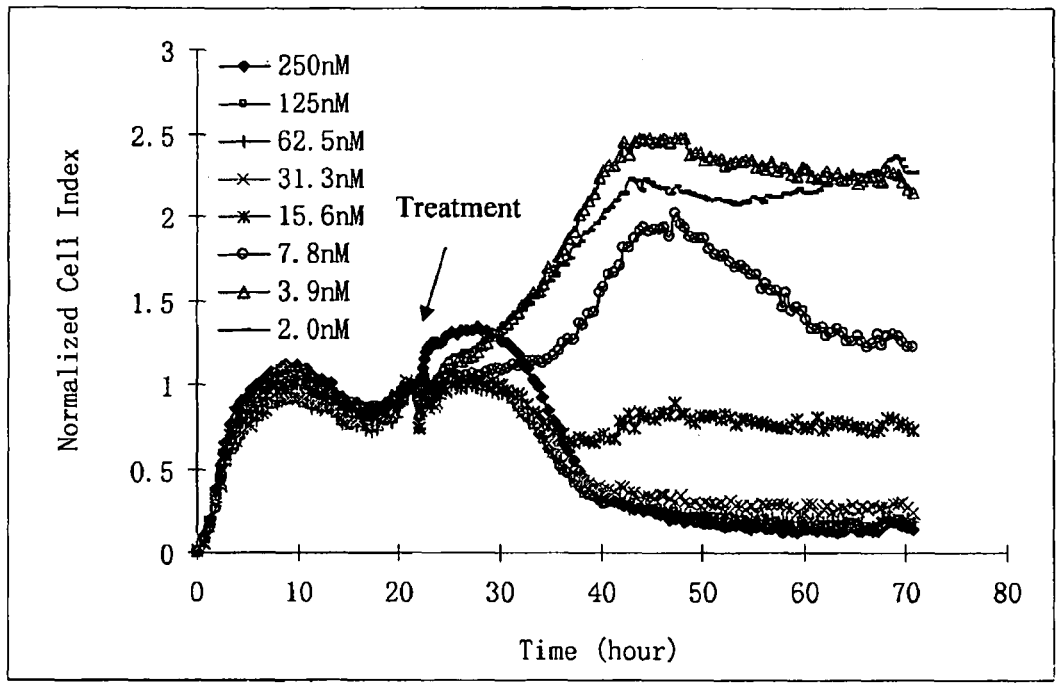
Figure 11:
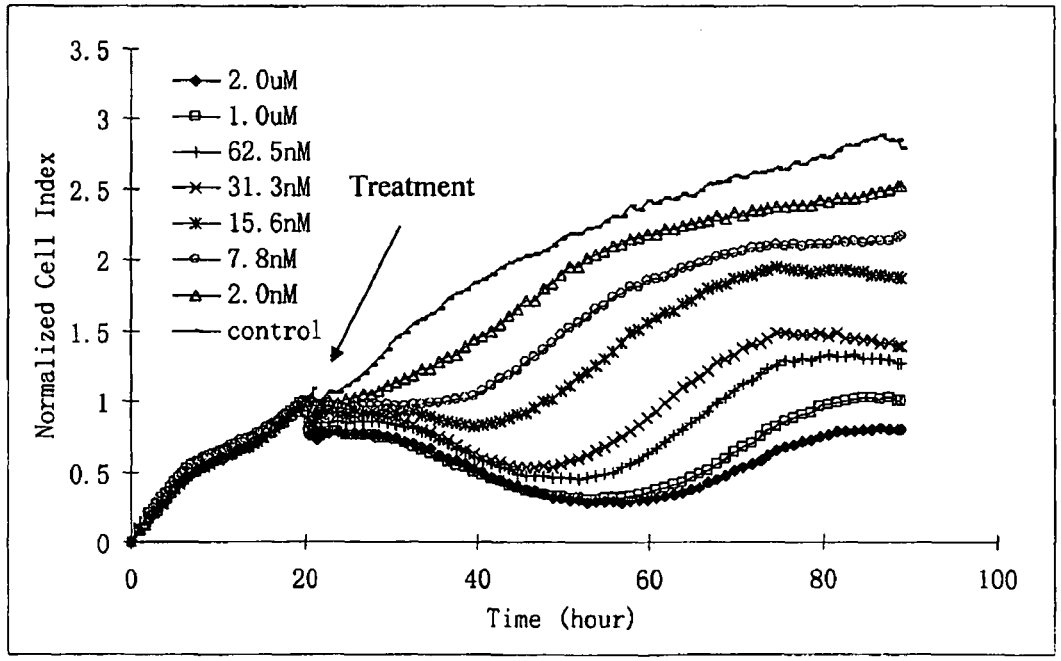
Figure 11:
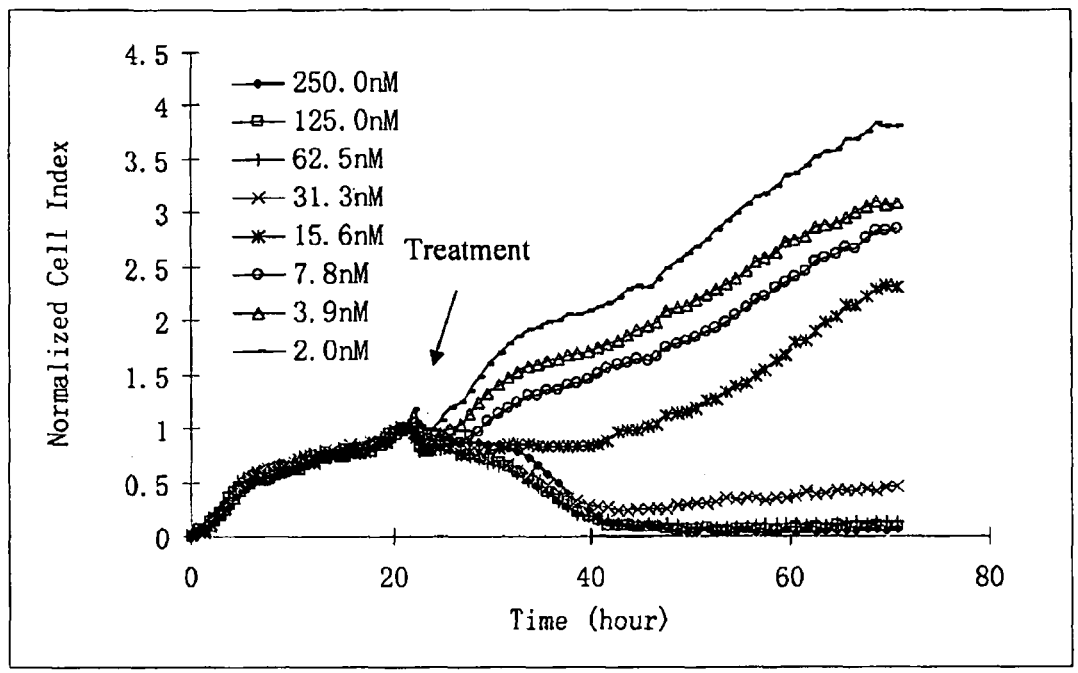
Figure 11:
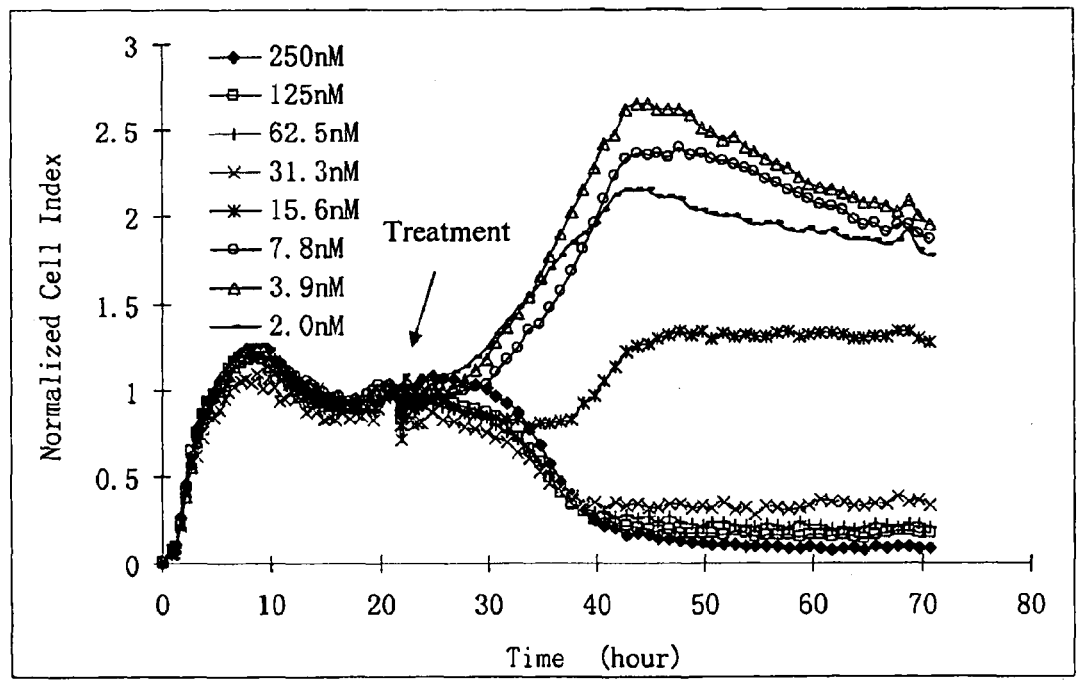
Figure 11E:
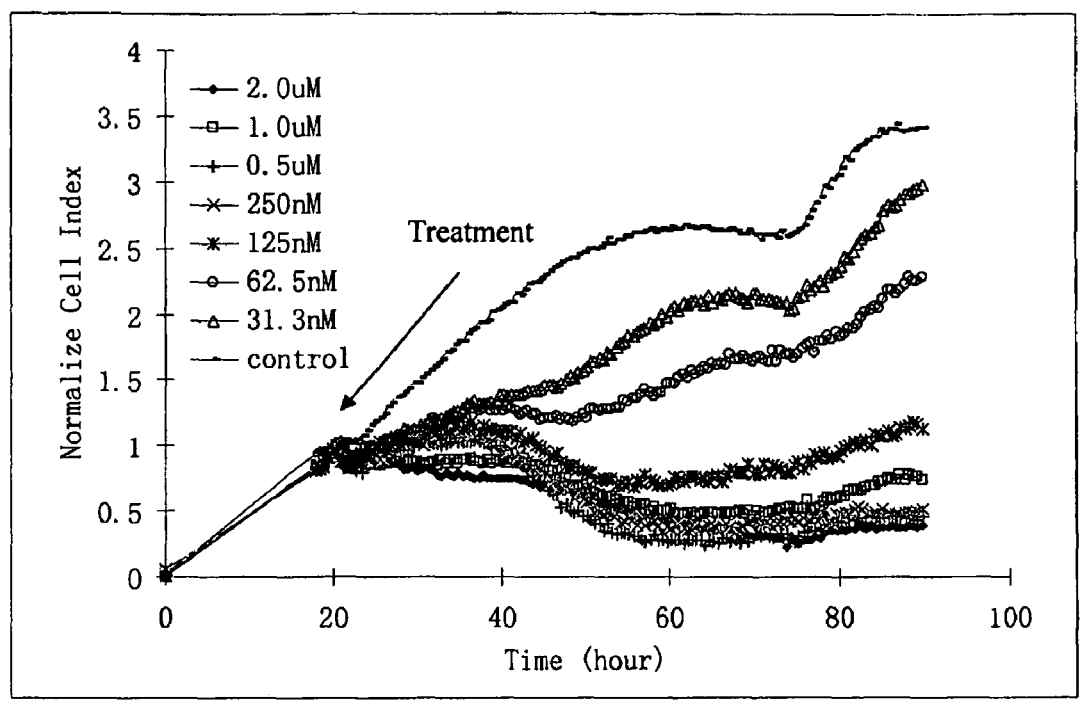

FIG. 11. shows the time-dependent cell index for a number of cell lines prior to and after addition of ACEA100160 at various concentrations: (A) MCF7adr (human breast adenocarcinoma), (B) PC3 (human prostate cancer), (C) KB (human head-neck cancer), (D) KB200 (human oral epithelioma) and (E) Bcap37 (human breast adenocarcinoma).

Figure 12:
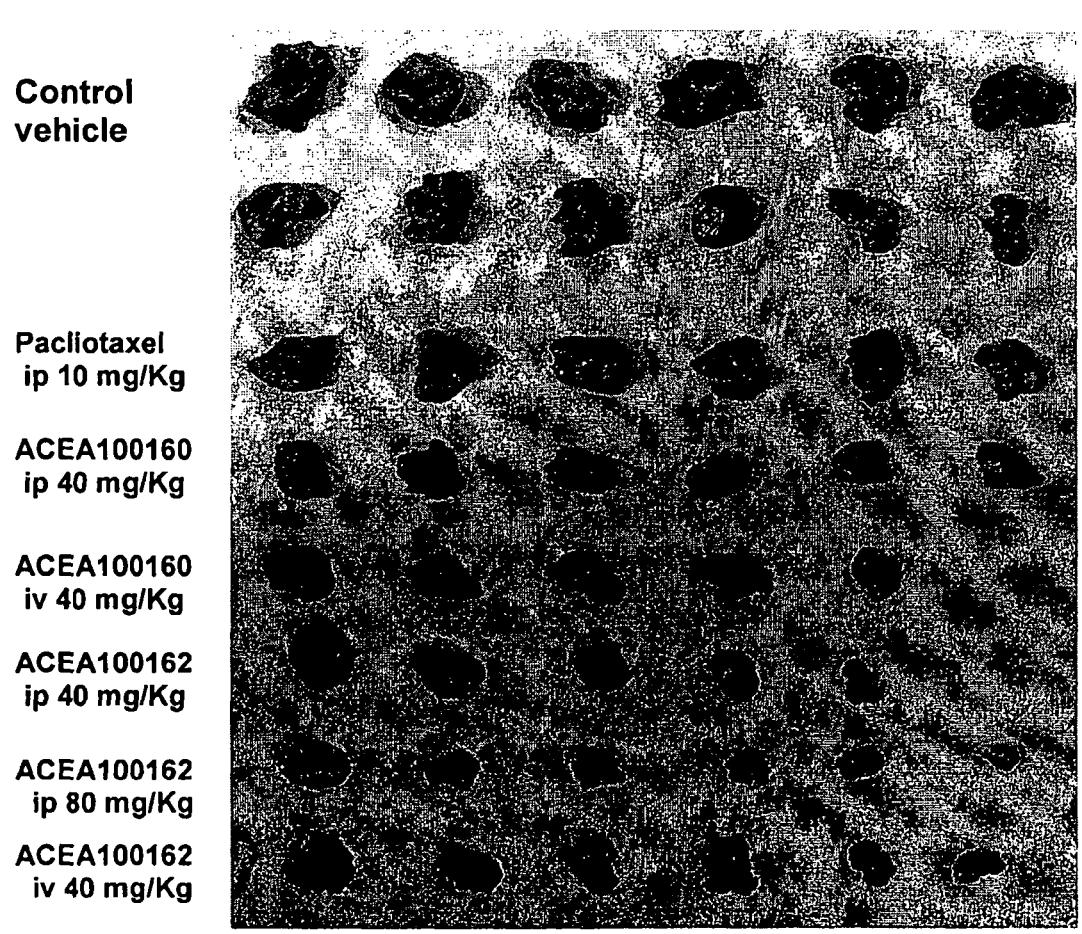

FIG. 12 shows Tumor growth suppression by ACEA100160 and ACEA100162 treated on mouse S180 carcinoma model. Animals were treated with ACEA100160 and ACEA100162 for 9 days.

Figure 13:
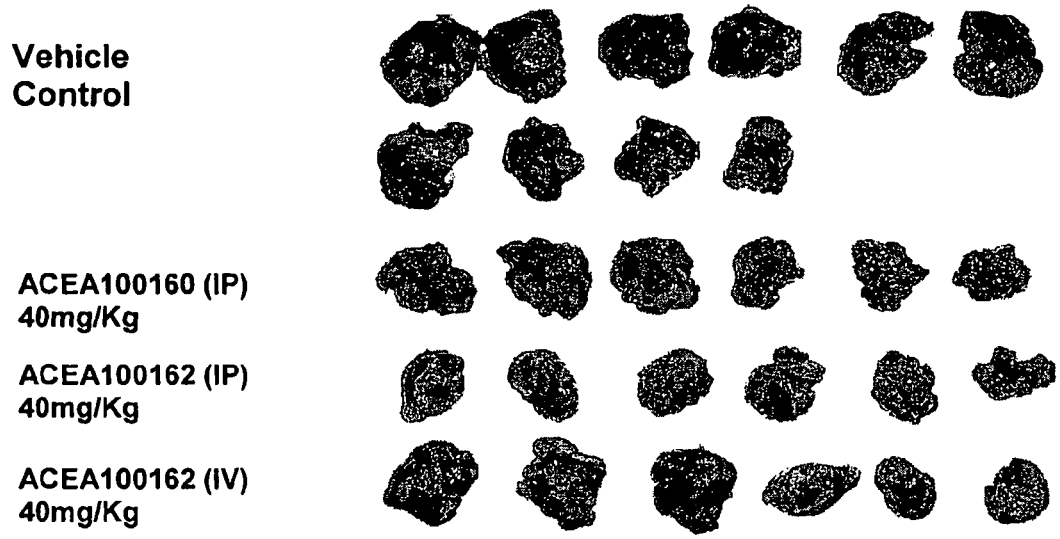

FIG. 13 shows Tumor growth suppression by ACEA100160 and ACEA100162 treated on mouse lewis lung cancer model. Animals were treated with ACEA100160 and ACEA100162 for 12 days.

EMBODIMENTS OF THE INVENTION

For clarity of disclosure, and not by way of limitation, the following description of selected embodiments of invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition incorporated herein by reference.

As used herein, "a" or "an" means "at least one" or "one or more".

The term "alkyl" as used herein refers to saturated hydrocarbon groups in a straight, branched, or cyclic configuration and particularly contemplated alkyl groups include lower alkyl groups (i.e., those having ten or less carbon atoms). Exemplary alkyl groups are methyl, ethyl, propyl, isopropyl, butyl, sec-butyl, tertiary butyl, pentyl, isopentyl, hexyl, etc. The term "alkenyl" as used herein refers to an alkyl as defined above and having at least one double bond. Thus, particularly contemplated alkenyl groups include straight, branched, or cyclic alkenyl groups having two to ten carbon atoms (e.g., ethenyl, propenyl, butenyl, pentenyl, etc.). Similarly, the term "alkynyl" as used herein refers to an alkyl or alkenyl as defined above and having at least one triple bond. Especially contemplated alkynyls include straight, branched, or cyclic alkynes having two to ten total carbon atoms (e.g., ethynyl, propynyl, butynyl, etc.).

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. Cycloalkyls also include one or two double bonds, which form the "cycloalkenyl" groups. Cycloalkyl groups are also further substituted by alkyl, alkenyl, alkynyl, halo and other general groups.

The term "aryl" or "aromatic moiety" as used herein refers to an aromatic ring system, which may further include one or more non-carbon atoms. Thus, contemplated aryl groups include (e.g., phenyl, naphthyl, etc.) and pyridyl. Further contemplated aryl groups may be fused (i.e., covalently bound with 2 atoms on the first aromatic ring) with one or two 5- or 6-membered aryl or heterocyclic group, and are thus termed "fused aryl" or "fused aromatic".

As also used herein, the terms "heterocycle", "cycloheteroalkyl", and "heterocyclic moieties" are used interchangeably herein and refer to any compound in which a plurality of atoms form a ring via a plurality of covalent bonds, wherein the ring includes at least one atom other than a carbon atom. Particularly contemplated heterocyclic bases include 5- and 6-membered rings with nitrogen, sulfur, or oxygen as the non-carbon atom (e.g., imidazole, pyrrole, triazole, dihydropyrimidine, indole, pyridine, thiazole, tetrazole etc.). Further contemplated heterocycles may be fused (i.e., covalently bound with two atoms on the first heterocyclic ring) to one or two ring or heterocycle, and are thus termed "fused heterocycle" or "fused heterocyclic base" or "fused heterocyclic moieties" as used herein.

As also used herein, the terms "imidazothiazole" or "imidazo-imidazole" or "imidazooxazole" herein refer to any compound in which the two designated heterocyclic rings are fused by any two adjacent atoms on the two heterocyclic rings.

The term "alkoxy" as used herein refers to straight or branched alkyl connecting to an oxygen atom called alkoxides, wherein the hydrocarbon portion may have any number of carbon atoms, may further include a double or triple bond and may include one or two oxygen, sulfur or nitrogen atoms in the alkyl chains. For example, suitable alkoxy groups include methoxy, ethoxy, propyloxy, isopropoxy, methoxyethoxy, etc. Similarly, the term "alkylthio" refers to straight or branched chain alkylsulfides, wherein the hydrocarbon portion may have any number of carbon atoms, may further include a double or triple bond and may include one or two oxygen, sulfur or nitrogen atoms in the alkyl chains. For example, contemplated alkylthio groups include methylthio, ethylthio, isopropylthio, methoxyethylthio, etc.

Likewise, the term "alkylamino" refers to straight or branched alkylamines, wherein the amino nitrogen "N" can be substituted by one or two alkyls and the hydrocarbon portion may have any number of carbon atoms and may further include a double or triple bond. Furthermore, the hydrogen of the alkylamino may be substituted with another alkyl group. Therefore, exemplary alkylamino groups include methylamino, dimethylamino, ethylamino, diethylamino, etc.

The term "aryloxy" as used herein refers to an aryl group connecting to an oxygen atom, wherein the aryl group may be further substituted. For example suitable aryloxy groups include phenyloxy, etc. Similarly, the term "arylthio" as used herein refers to an aryl group connecting to a sulfur atom, wherein the aryl group may be further substituted. For example suitable arylthio groups include phenylthio, etc.

The term "halogen" as used herein refers to fluorine, chlorine, bromine and iodine.

It should further be recognized that all of the above-defined groups may further be substituted with one or more substituents, which may in turn be substituted as well. For example, a hydrogen atom in an alkyl or aryl is substituted with an amino, halo or other groups.

The term "substituted" as used herein refers to a replacement of an H atom with another atom or group. Alkyl, alkenyl and alkynyl groups are often substituted to the extent that such substitution makes sense chemically. Typical substituents include, but are not limited to, halo, =O, =N—CN, =N—OR, =NR, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including C1-C8 alkyl, C2-C8 alkenyl, C2-C8 alkynyl, C3-C8 cycloalkyl, C5-C12 aryl, C1-C8 acyl, and heteroforms of these, each of which can itself be further substituted with appropriate substituents; other substituents for aryl and heteroaryl moieties include halo, O((CH2)pO)qR, where each p is independently 1-4 and q is 1-6, OR, NR2, SR, SO2R, SO2NR2, NRSO2R, NRCONR2, NRCOOR, NRCOR, CN, COOR, CONR2, OOCR, COR, and NO2, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C3-C8 cycloalkyl, C3-C8 heterocyclyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group may of course be further substituted with the groups described herein as suitable for each type of such substituents or for each component of the substituent; and such substituents can be substituted with one or more substituents selected from halo, $CF_3$, C1-4 alkyl and C1-4 alkoxy. Thus, for example, an arylalkyl substituent may be substituted on the aryl portion with substituents described herein as typical for aryl groups, and it may be further substituted on the alkyl portion with substituents described herein as typical or suitable for alkyl groups. Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups can be described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy. Alternatively, such groups can be otherwise described, e.g. as a C5-C6-aryl-C1-C2-alkyl, which would refer to a 5-6 membered aryl ring connected to the base molecule through a C1-C2 linker.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain. Thus —CH(Me)- and —$C(Me)_2$- may also be referred to as alkylenes, as can a cyclic group such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

Particularly contemplated functional groups include nucleophilic groups (e.g., —$NH_2$, —OH, —SH, —NC, etc.), electrophilic groups (e.g., C(O)OR, C(X) OH, etc.), polar groups (e.g., —OH), non-polar groups (e.g., heterocycle, aryl, alkyl, alkenyl, alkynyl, etc.), ionic groups (e.g., —$NH_3^+$), and halogens (e.g., —F, —Cl), NHCOR, $NHCONH_2$, $OCH_2COOH$, $OCH_2CONH_2$, $OCH_2CONHR$, $NHCH_2COOH$, $NHCH_2CONH_2$, $NHSO_2R$, $OCH_2$-heterocycles, PO₃H, SO₃H, amino acids, and all chemically reasonable combinations thereof. Moreover, the term "substituted" also includes multiple degrees of substitution, and where multiple substituents are disclosed or claimed, the substituted compound can be independently substituted by one or more of the disclosed or claimed substituent moieties. Furthermore, the term "mono-/di-/tri-/tetra-substituted" used herein refers to one, or two, or three or four functional groups described above that substituted onto the aromatic or heterocyclic or fused aromatic or heterocyclic moiety, in which such multi-functional groups are substituted at the combination of any ortho- or para- or meta-position of the aromatic or heterocyclic moiety.

In some preferred embodiments, $W^2$ is S and $W^3$ is N. IN certain embodiments, $W^5$ is S. In some embodiments, A is $NR^4$.

In many embodiments, Z is $CH_2$-Phenyl or Phenyl, where the phenyl ring is optionally substituted. Preferred phenyl substituents in these embodiments include halo, C1-C4 alkoxy, OH, C1-C4 alkyl, or C1-C4 alkyl substituted with =O or with one or more F, Cl, CN, $CF_3$, Br, NRR, COOR, and CONRR, where R is as defined for the preferred Z group structures shown above.

B. Heterocyclic Compounds and Pharmaceutical Compositions Thereof

B.1. Representative Compounds:

Some representative compounds are listed in Tables 1-7. Some representative compounds are listed in Tables 1-7.

TABLE 1

Representative substituted thiazole imidazothiazole derivatives.

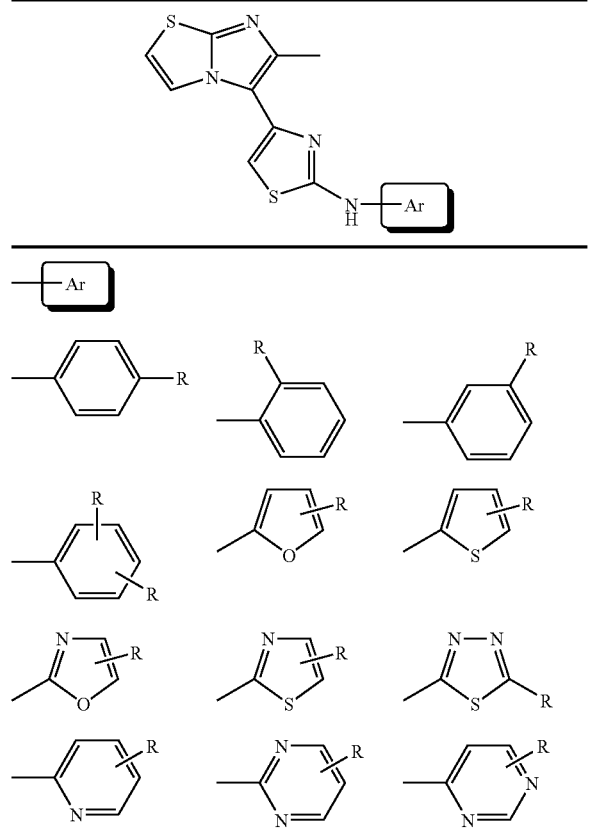

TABLE 1-continued

Representative substituted thiazole imidazothiazole derivatives.

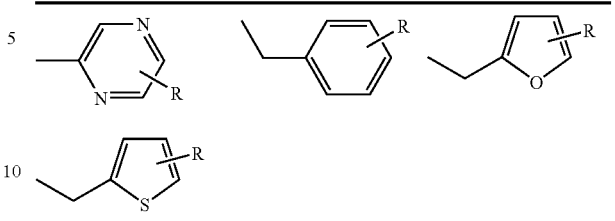

R=H, F, Cl, Br, I, Me, Et, Propyl, Bu, $CF_3$, OMe, OEt, OiPr, $OCF_3$, $COCH_3$, NO2, $NMe_2$, $NEt_2$, NHCOMe, $SO_2NH_2$, $SO_2NHPh$, $SO_2NH$-thiazole, $SO_2NH$-oxazole, $SO_2NH$-pyridine, $NH_2$, OH, SMe, SEt.

TABLE 2

Representative substituted thiazole imidazopyrimidine derivatives.

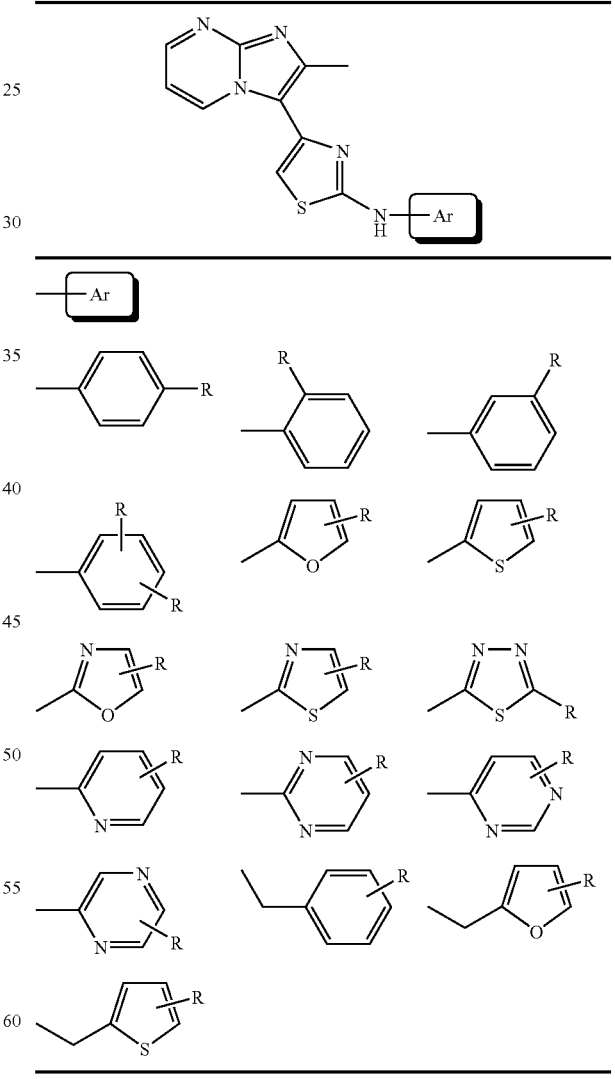

R=H, F, Cl, Br, I, Me, Et, Propyl, Bu, $CF_3$, OMe, OEt, OiPr, $OCF_3$, $COCH_3$, NO2, $NMe_2$, $NEt_2$, NHCOMe, $SO_2NH_2$, $SO_2NHPh$, $SO_2NH$-thiazole, $SO_2NH$-oxazole, $SO_2NH$-pyridine, $NH_2$, OH, SMe, SEt.

TABLE 3
Representative fluoro-substituted derivatives
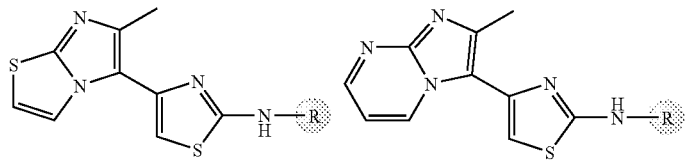
HN—R =
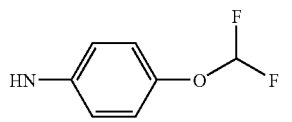 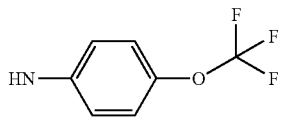
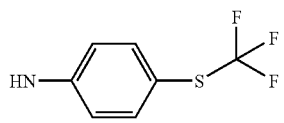 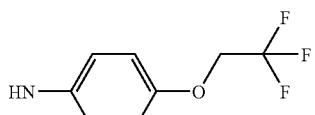
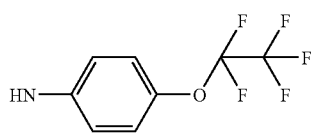 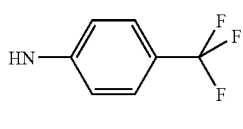
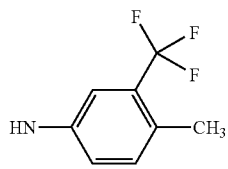 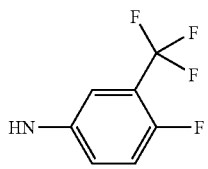
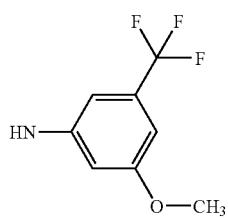 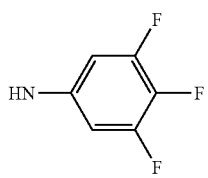
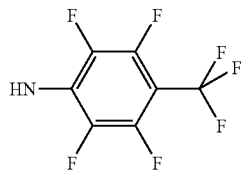 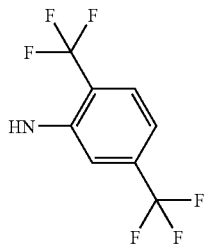
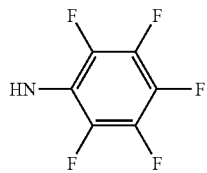 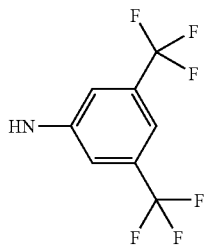

TABLE 3-continued

Representative fluoro-substituted derivatives

TABLE 4

Representative substituted alkoxy ether compounds.

TABLE 4-continued
Representative substituted alkoxy ether compounds.
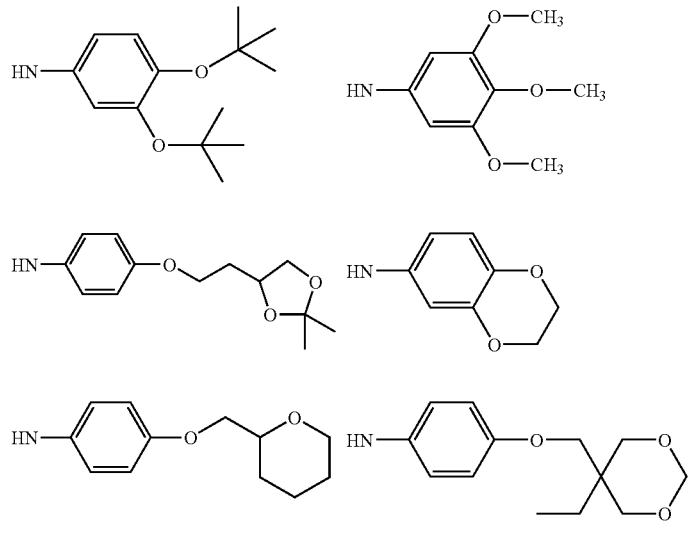
TABLE 5
Representative methoxy PEG unit substituted compounds.
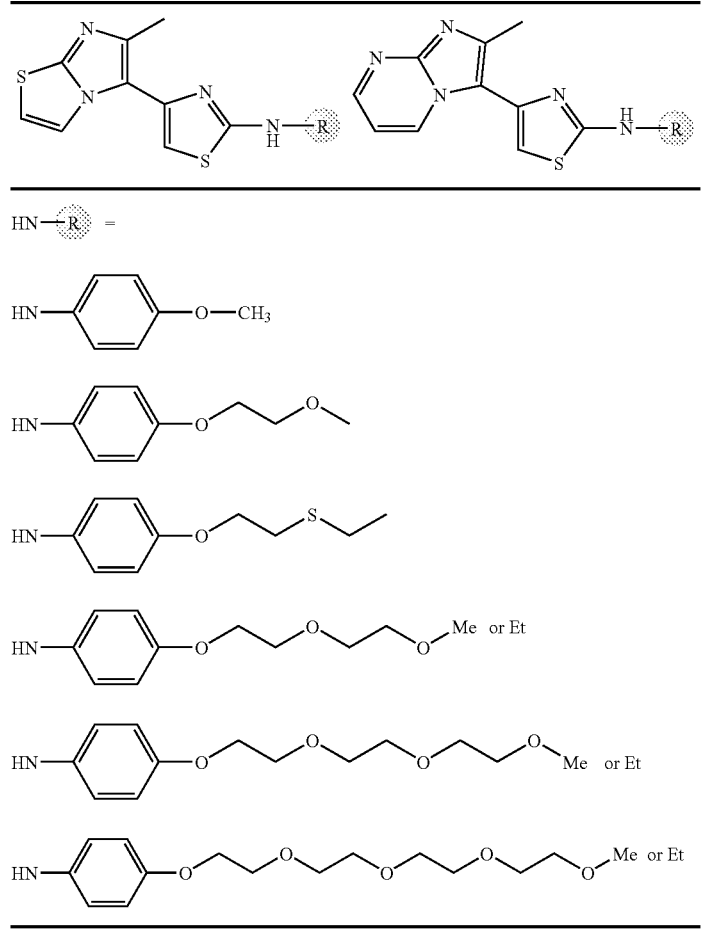

TABLE 6
Representative PEG unit substituted compounds.
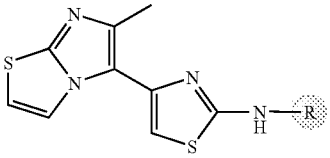
TABLE 7
Representative cyclic unit substituted compounds.
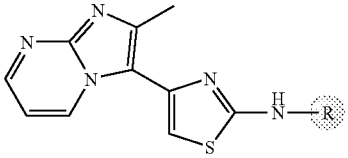

TABLE 7-continued

Representative cyclic unit substituted compounds.

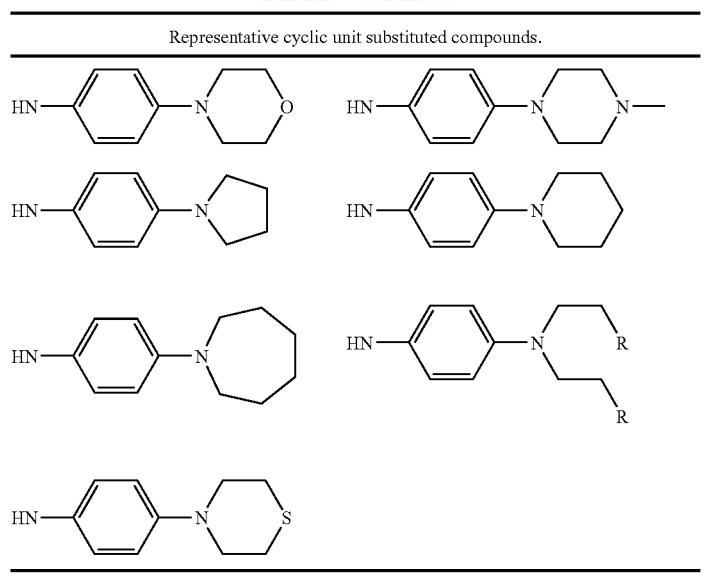

B.2. Exemplary Synthesis:

The exemplary compounds were synthesized by routes as illustrated in Schemes I, II, and IV. Known methods from the art can be used and modified by those skilled in the art to produce the compounds of the invention from available starting materials. Additional synthesis methods for compounds within the scope of the invention are disclosed, for example, in Hayakawa et al., *Biorg. Med. Chem.* Vol. 15, 403-12 (2007); Ermolat'ev, et al., *J. Comb. Chem.* Vol. 8, 659-63 (2006); Carballares, et al., *Tetrahedron Lett.* vol. 48, 2041-45 (2007); and Rupert, et al., *Biorg. Med. Chem. Lett.*, vol. 13, 347-50 (2003).

Scheme I. Synthesis of thiazole imidazopyrimidine derivatives

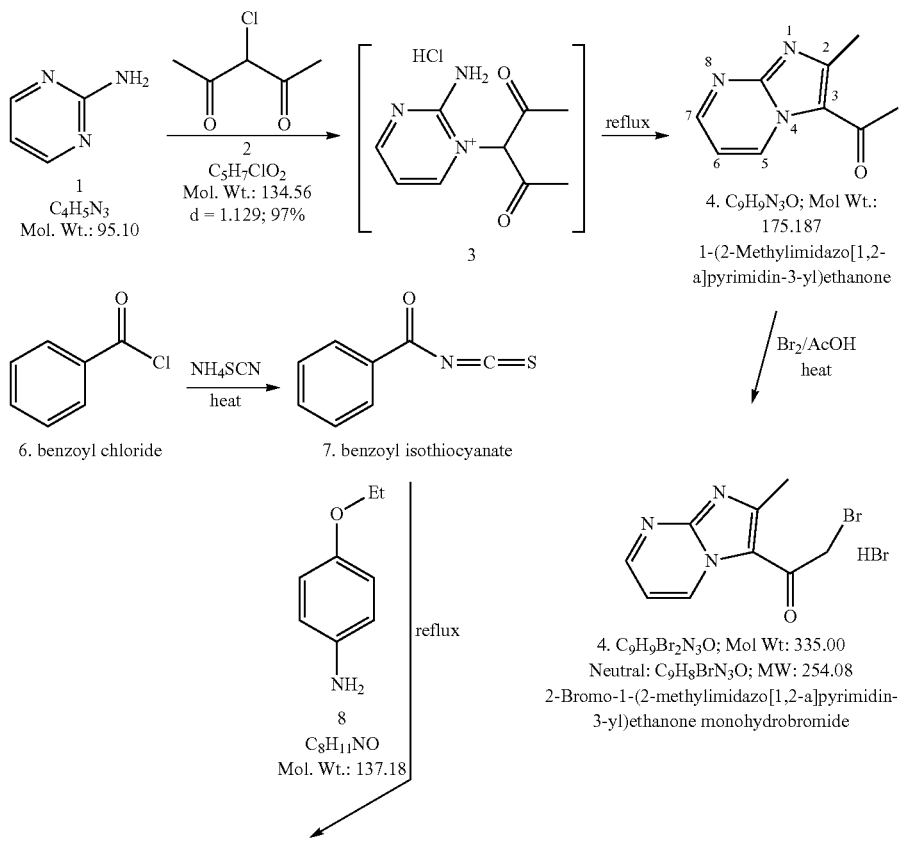

-continued

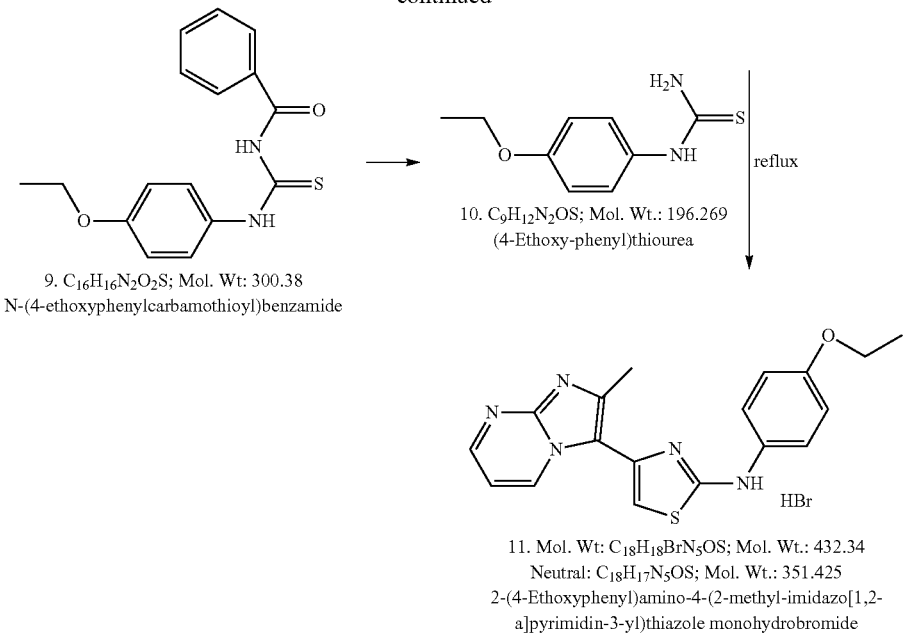

9. C$_{16}$H$_{16}$N$_2$O$_2$S; Mol. Wt: 300.38
N-(4-ethoxyphenylcarbamothioyl)benzamide 10. C$_9$H$_{12}$N$_2$OS; Mol. Wt.: 196.269
(4-Ethoxy-phenyl)thiourea 11. Mol. Wt: C$_{18}$H$_{18}$BrN$_5$OS; Mol. Wt.: 432.34
Neutral: C$_{18}$H$_{17}$N$_5$OS; Mol. Wt.: 351.425
2-(4-Ethoxyphenyl)amino-4-(2-methyl-imidazo[1,2-a]pyrimidin-3-yl)thiazole monohydrobromide Synthesis of 1-(2-methylimidazol[1,2-a]pyrimidin-3-yl)ethanone (4)

3-Chloro-2,5-pentanedione (2) (106 mL, 119 g, 887 mmol, 1.2 eq) was dissolved in 650 mL of anhydrous ethanol. 2-Aminopyrimidine (1) (71.5 g×97%=69.36 g, 729 mmol) was added to above stirred solution. The resulting mixture was refluxed for 40 h at an oil bath temperature of 100-105° C. The black reaction mixture was cooled and concentrated under reduced pressure. The residue was treated with saturated sodium bicarbonate solution (~500 mL) in portions, and swelled the flask to mix well. The mixture was extracted with dichloromethane (×6). The extracts were washed with sodium bicarbonate solution and brine. The organic phase was dried and concentrated. The residue was purified by flash chromatography on a silica gel column (7×30 cm) by gradient elution using n-hexane-ethyl acetate (3:1, 2:1, 1:1, 1:2 and 0:1) and then dichloromethane-methanol (30:1, 20:1, 10:1 and 5:1). The product fractions were collected (TLC, R$_f$ 0.36, 100% ethyl acetate) and concentrated providing a light black solid. Other fractions contained products were collected and re-purified again by the same way. 27.84 g (21.8%) of the final product was obtained. Portion of the product was re-crystallized from small amount of acetonitrile to give red to light brown crystals 4, m.p. 255.6-256.6° C. $^1$H NMR (CDCl$_3$) δ 2.65 (s, 3H, 3-COCH$_3$), 2.86 (s, 3H, 2-CH$_3$), 7.04-7.12 (m, 1H, 6-H), 7.70-7.74 (m, 1H), 9.96-10.00 (m, 1H).

Synthesis of 2-bromo-1-(2-methylimidazo[1,2-a]pyrimidin-3-yl)ethanone monohydrobromide (5) (bromination)

1-(2-methylimidazol[1,2-a]pyrimidin-3-yl)ethanone (4) (1.75 g, 10 mmol) was dissolved in 20 mL of glacial acetic acid by gently warming the flask, which was then cooled to room temperature. A solution of bromine (0.6 mL, 1.85 g, 11.5 mmol, 1.15 eq) in 4 mL of acetic acid was added slowly to the above stirred reaction mixture at room temperature for more than 30 min. [Caution: bromine is highly corrosive. Handling bromine needs to be done very carefully in the well ventilated fume hood. Long gloves or double gloves are needed for operator. Absolutely avoid splash onto skin or breathe the vapor]. Some solid precipitated out before completing the addition. The reaction mixture was stirred at an oil bath temperature of 100-110° C. for 3 hours, and then stirred at room temperature overnight. The solid was filtered and washed several times with acetone, occasionally washed with anhydrous ethanol in the middle of acetone wash. The light brown solid was taken up with acetone containing small amount of ethanol, and the mixture was stirred at room temperature for more than 5 hours. The solid was filtered, and the solid was washed as mentioned above (one more taken up and wash cycle is recommended for larger scale). After dried under vacuum, 2.43 g (72.5%) pale brown powder solid product 5 was obtained as the monohydrobromide salt. Decomposed at above 250° C. TLC, R$_f$ 0.42 (100% ethyl acetate). $^1$HNMR (DMSO-d$_6$) δ 2.82 (s, 3H, 2-CH$_3$), 4.83 (s, 2H, CH$_2$Br), 7.40-7.50 (m, 1H), 8.80-8.90 (m, 1H), 9.82-9.90 (m, 1H).

Synthesis of 1-benzoyl-3-[4-(ethoxyphenyl)]thiourea (9)

[References: ARKIVOC 2003, 434-442; Bioorg. Med. Chem. 2000, 2663]. Benzoyl chloride (6) (14.0 mL, 16.95 g, 120 mmol) was added dropwise at room temperature to a stirred solution of ammonium thiocyanate (10.26 g, 135 mmol, 1.125 eq) in 100 mL of acetone. Some white solid precipitated out. The reaction mixture was heated to reflux for 5 min (oil temperature ~65-70° C.). Thus obtained benzoyl isothiocyanate (7) was used directly to the next step without purification. A solution of 4-ethoxyaniline (8) (17.0 mL, 18.1 g, 132 mmol, 1.1 eq) in 25 mL of acetone was added slowly to the above stirred reaction mixture while it is still in the oil bath (65-70° C.). The addition needs to be done very slowly for ~1 h considering the exothermic reaction. A lot of white solid precipitated out. The reaction mixture was swelled by hands and further refluxed for 5 min. The cooled reaction mixture was poured into ice water. The solid was filtered and washed 3 times with water. The solid was re-crystallized from ethanol (~1.6 L) to provide the desired product 9 as light yellow, long needles, yield 36 g (99%), m.p. 151.0-153.5° C.

Synthesis of (p-ethoxyphenyl)thiourea (10)

Sodium hydroxide aqueous solution (1 M, 60 mL, 60 mmol, 1.2 eq) was added to a stirred mixture of 1-benzoyl-3-[4-(ethoxyphenyl)]thiourea (9) (16.5 g, 55 mmol) in 350 mL of ethanol. The reaction mixture was refluxed for 1 h, cooled and concentrated. The white solid was treated with water (~200 mL). The solid was filtered and washed with water. The crude crystalline product was re-crystallized from ethanol, filtered and dried under vacuum providing 7.66 g (71.0%) desired product 10, m.p. 176.5-178.5° C. TLC, $R_f$ 0.45 (n-hexane-ethyl acetate: 1:1). $^1$HNMR (DMSO-$d_6$) δ 1.31 (t, 3H, J=6.8 Hz), 4.00 (q, 2H, J=6.8 Hz), 6.80-6.90 (m, 2H), 7.15-7.25 (m, 2H), 9.50 (s, 1H, NH).

Synthesis of 2-(4-ethoxyphenylamino)-4-(2-methyl-imidazo[1,2-a]pyrimidin-3-yl)thiazole monohydrobromide (11) (cyclization into thiazole ring)

A mixture of 2-bromo-1-(2-methylimidazo[1,2-a]pyrimidin-3-yl)ethanone monohydrobromide (5) (2.43 g, 7.25 mmol) and (p-ethoxyphenyl)thiourea (10) (1.40 g, 7.1 mmol) in 140 mL of anhydrous ethanol was refluxed under stirring for 15 h (oil bath temperature ~105° C.). It was then stirred at room temperature for 6 h or overnight. The solid was filtered and washed with acetone. The crude soft crystals were taken up with acetone-ethanol (3:1) and stirred at room temperature for more than 6 h or overnight. The solid was filtered and washed as above. The crude product was taken up with acetone-ethanol (3:1) and stirred at room temperature for more than 6 h. The crude product was filtered, washed, and re-crystallized from methanol. The methanol solution was filtered while hot to remove black dust, and then heated into solution. The yellow crystals was filtered and washed. It was re-crystallized two more times from methanol, and dried under vacuum to provide the desired product 11 as long, soft yellow needles, yield 1.55 g (50.5%), decomposed at above 240° C. TLC $R_f$ 0.32 (dichloromethane-methanol: 20:1); $R_f$ 0.46 (dichloromethane-methanol containing: 20:1 containing 1% ammonium hydroxide aqueous solution); $R_f$ 0.30 (100% ethyl acetate ×2). HPLC purity: 99%. $^1$HNMR (DMSO-$d_6$) δ 1.32 (t, 3H, J=6.8 Hz), 2.67 (s, 3H), 4.00 (q, 2H, J=6.8 Hz), 6.90-6.95 (m, 2H), 7.35 (s, 1H), 7.49-7.52 (m, 2H), 7.61-7.67 (m, 1H), 8.94-8.97 (m, 1H), 9.57 (d, 1H, J=6.8 Hz), 10.28 (s, 1H, NH). ESI-MS, m/z 352 (M+1)$^+$.

The representative derivatives listed in Tables 2-7 are readily synthesized utilizing similar procedures from known or readily available starting materials.

Preparation of Neutral Compound from Compound 11 (HBr Salt).

The HBr salt was suspended in methanol, and the excess amount of sodium bicarbonate was added with vigorous stirring until the suspended compound salt was completely dissolved. Excess amount of inorganic salt was filtered off. The solution was concentrated, and the residue was recrystallized from methanol to provide pale yellow crystalline material as the neutral compound.

Preparation of Different Salts.

The neutral compound obtained and 1 equivalent amount of the selected acids. The solution was concentrated, and the residue was recrystallized from alcohol to give the desired salts with the selected anions as described above.

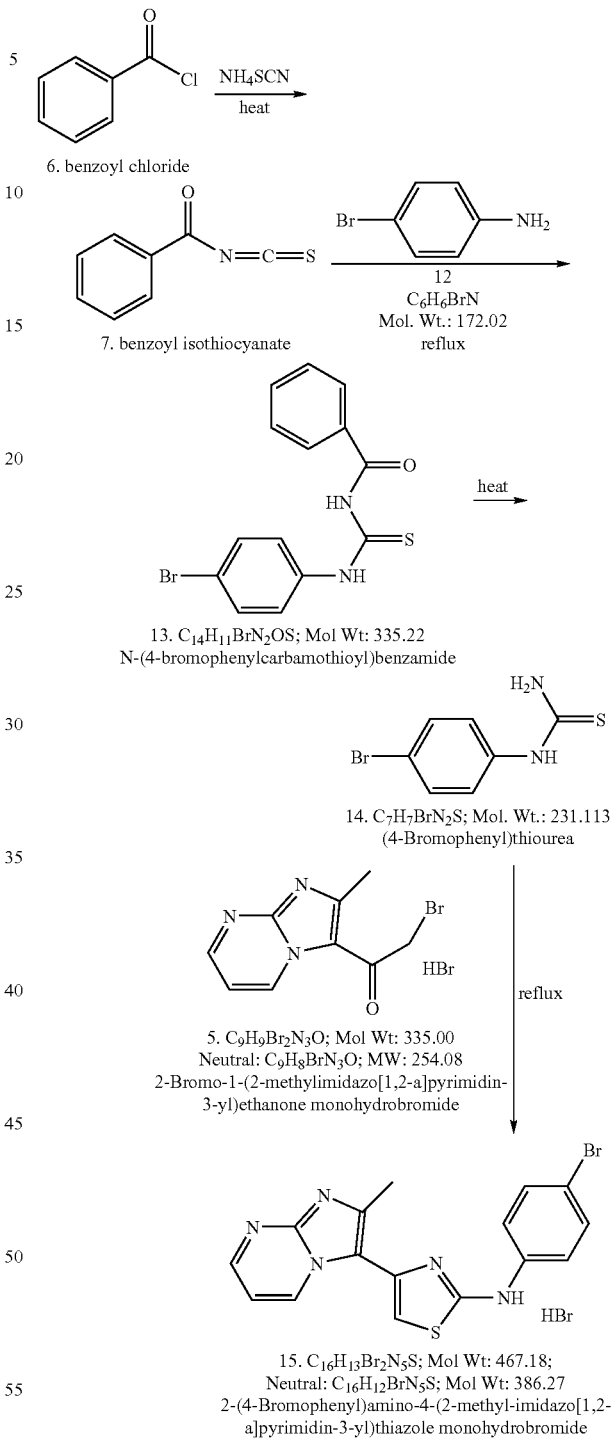

Scheme II. Synthesis of new thiazole imidazopyrimidine derivative 6. benzoyl chloride 7. benzoyl isothiocyanate 13. C$_{14}$H$_{11}$BrN$_2$OS; Mol Wt: 335.22
N-(4-bromophenylcarbamothioyl)benzamide 14. C$_7$H$_7$BrN$_2$S; Mol. Wt.: 231.113
(4-Bromophenyl)thiourea 5. C$_9$H$_9$Br$_2$N$_3$O; Mol Wt: 335.00
Neutral: C$_9$H$_8$BrN$_3$O; MW: 254.08
2-Bromo-1-(2-methylimidazo[1,2-a]pyrimidin-3-yl)ethanone monohydrobromide 15. C$_{16}$H$_{13}$Br$_2$N$_5$S; Mol Wt: 467.18;
Neutral: C$_{16}$H$_{12}$BrN$_5$S; Mol Wt: 386.27
2-(4-Bromophenyl)amino-4-(2-methyl-imidazo[1,2-a]pyrimidin-3-yl)thiazole monohydrobromide Synthesis of 1-benzoyl-3-[4-(bromophenyl)]thiourea (13)

Benzoyl chloride (6) (14.0 mL, 16.95 g, 120 mmol) was added dropwise at room temperature to a stirred solution of ammonium thiocyanate (10.26 g, 135 mmol, 1.125 eq) in 100 mL of acetone. Some white solid precipitated out. The reaction mixture was heated to reflux for 5 min (oil temperature ~65-70° C.). Thus obtained benzoyl isothiocyanate (7) was used directly to the next step without purification. A solution of 4-bromoaniline (12) (22.71 g, 132 mmol, 1.1 eq) in 50 mL of acetone was added slowly to the above stirred reaction mixture while it is still in the oil bath (65-70° C.). The addition needs to be done very slowly for ~1 h considering the exothermic reaction. A lot of white solid precipitated out. The reaction mixture was swelled by hands and further refluxed for 5 min. The cooled reaction mixture was poured into ice water. The solid was filtered and washed 3 times with water. The solid was re-crystallized from ethanol (~2 L) to provide the desired product 13 as light yellow crystals, yield 32.2 g (80.5%), m.p. 150.0-152.7° C.

Synthesis of (p-bromophenyl)thiourea (14)

Sodium hydroxide aqueous solution (1 M, 96 mL, 96 mmol, 1.2 eq) was added to a stirred mixture of 1-benzoyl-3-[4-(bromophenyl)]thiourea (13) (26.72 g, 80 mmol) in 500 mL of ethanol. The reaction mixture was refluxed for 1 h, cooled and concentrated. The white solid was treated with water (~300 mL). The solid was filtered and washed with water. The crude crystalline product was re-crystallized from ethanol, filtered and dried under vacuum providing 12.7 g (70%) desired product 14, TLC, $R_f$ 0.45 (n-hexane-ethyl acetate: 1:1); m.p. 187.8-189.2° C.

Synthesis of 2-(4-bromophenylamino)-4-(2-methylimidazo[1,2-a]pyrimidin-3-yl)thiazole monohydrobromide (15) (cyclization into thiazole ring)

A mixture of 2-bromo-1-(2-methylimidazo[1,2-a]pyrimidin-3-yl)ethanone monohydrobromide (5) (1.28 g, 3.8 mmol) and (p-bromophenyl)thiourea (14) (0.88 g, 3.8 mmol) in 80 mL of anhydrous ethanol was refluxed under stirring for 20 h (oil bath temperature ~105° C.). It was then stirred at room temperature for 6 h. The solid was filtered and washed with acetone. The crude soft crystals were taken up with acetone-ethanol (3:1) and stirred at room temperature for more than 6 h. The solid was filtered and washed as above. The crude product was taken up with acetone-ethanol (3:1) and stirred at room temperature for more than 6 h. The crude product was filtered, washed, and re-crystallized from methanol. The methanol solution was filtered while still hot to remove black dust, and then heated into solution. The crude product was filtered and washed. It was re-crystallized two more times methanol, and dried under vacuum to provide the desired product 15 as light yellow crystals yield 1.448 g (81%). TLC $R_f$ 0.25 (dichloromethane-methanol: 20:1); $R_f$ 0.28 (100% ethyl acetate, ×2). $^1$HNMR (DMSO-$d_6$) δ 2.67 (s, 3H), 3.17 (s, 2H), 7.45 (s, 1H), 7.48-7.53 (m, 2H), 7.58-7.64 (m, 3H), 8.94 (d, 1H, J=3.6 Hz), 9.46-9.50 (m, 1H), 10.65 (s, 1H, NH). ESI-MS, m/z 386 (M)$^+$, 388 (M+1)$^+$.

The representative derivatives listed in Tables 2-7 are readily synthesized utilizing similar procedures from known or readily available starting materials.

The neutral compound was prepared as described above.

Other salts were prepared as described above.

The compounds of the invention can be prepared by modifications of known synthetic methods from known or available starting materials. Some exemplary compounds are synthesized as illustrated in Schemes III and IV. Additional methods that may be used to make the products or precursors for making them are disclosed in, for example, Andreani, et al., *J. Med. Chem.* vol. 49, 7897-7901 (2006); Nafziger, et al., *Cytotechnology*, vol. 6, 227-32 (1991); Andreani, et al., *ARKIVOC* 2004(v) 76-84; Andreani, et al., *Bioorg. Med. Chem.*, vol. 8, 2359-66 (2000); Saldabol, et al., Engl. Transl. of *Khimiya Geterotsiklicheskikh Soedinenii*, no. 1, 55-61 (1975); Andreani, et al., *Collect. Czech. Chem. Commun.*, vol. 65, 267-79 (2000); and Andreani, et al., *Bioorg. Med. Chem.*, vol 12, 5525-32 (2004).

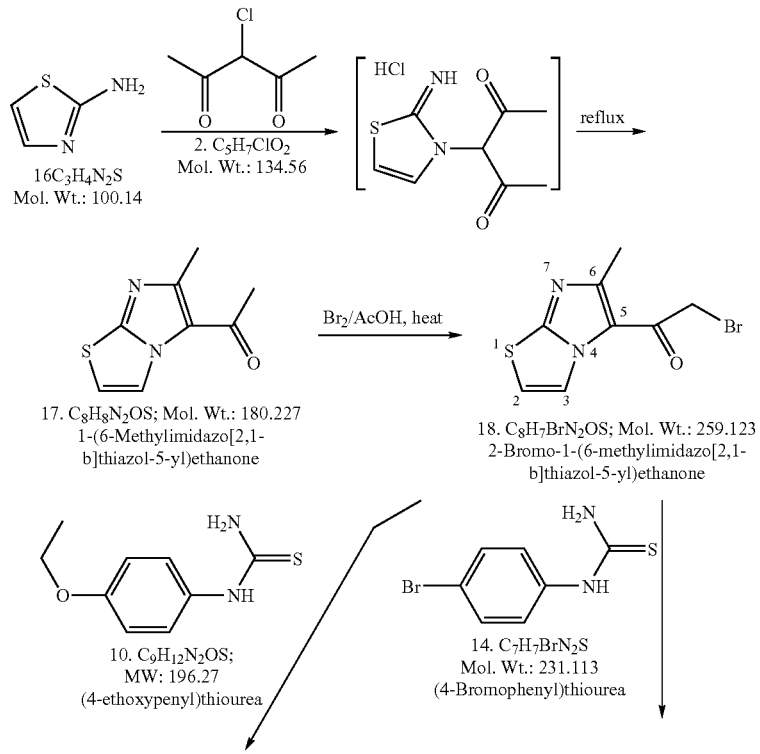

Scheme III. Synthesis of thiazole imidazothiazole derivatives

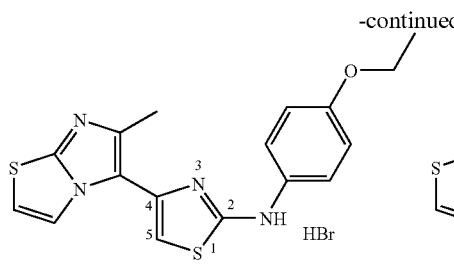

20. C₁₇H₁₇BrN₄OS₂; MW: 437.38
Neutral Mol: C₁₇H₁₆N₄OS₂; MW: 356.47
2-(4-ethoxyphenyl)-amino-4-(6-methylimidazo[2,1-b]thiazol-5-yl)thiazole

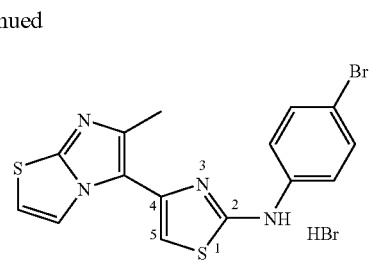

19. C₁₅H₁₂Br₂N₄S₂; MW: 472.22
Neutral Mol: C₁₅H₁₁BrN₄S₂; Mol. Wt.: 391.31
2-(4-Bromophenyl)amino-4-(6-methylimidazo[2,1-b]thiazol-5-yl)thiazole

Synthesis of 1-(6-Methylimidazo[2,1-b]thiazol-5-yl)ethanone (17)

2-Aminothiazole was recrystallized from anhydrous ethanol, filtered and dried before use. A solution of 2-aminothiazole (16) (20.9 g, 202.4 mmoL) and 3-Chloro-2,5-pentanedione (2) (33.7 g, 97%, 242.9 mmol, 1.2 eq) in 180 mL of anhydrous ethanol was refluxed for 72 h in an oil bath. The black reaction mixture was cooled and concentrated under reduced pressure. The residue was treated with saturated sodium bicarbonate solution in portions, and then extracted with dichloromethane. The organic phase was dried and concentrated. The residue was purified by flash chromatography on a silica gel column using dichloromethane-methanol (80:1). The product fractions were collected (TLC, $R_f$ 0.60 neutral form; $R_f$=0.5 salt form, dichloromethane-methanol 40:1) and concentrated providing white solid product 17 in 11.7% yield, 1.6 g neutral form and 3.2 g salt form. ¹H NMR (CDCl₃) δ 2.55 (s, 3H, 5-COCH₃), 2.70 (s, 3H, 6-CH₃), 6.78 (d, 1H, J=4.8 Hz), 8.39 (d, 1H, J=4.8 Hz).

Synthesis of 2-bromo-1-(6-methylimidazo[2,1-b]thiazol-5-yl)ethannone hydrobromide (18)

1-(6-Methylimidazo[2,1-b]thiazol-5-yl)ethanone (17) (0.54 g, 3.0 mmol) was dissolved in 7 mL of glacial acetic acid. A solution of bromine (0.18 mL, 0.56 g, 3.5 mmol) in 3 mL of glacial acetic acid was added slowly to above stirred solution in 30 min. Some yellow solid appeared. The mixture was heated to reflux under stirring for 3 h, and then stirred at room temperature overnight. The solid was filtered and washed three times with acetone, and stirring for 3-5 h for each wash was needed. The solid was filtered and dried under vacuum to provide 0.73 g (71.6%) white solid the desired product 18.

Synthesis of 2-(4-bromophenyl)amino-4-(6-methylimidazo[2,1-b]thiazol-5-yl)-thiazole monohydrobromide (19)

A mixture of 2-bromo-1-(6-methylimidazo[2,1-b]thiazol-5-yl)ethannone hydrobromide (18) (0.73 g, 2.0 mmol) and (p-bromophenyl)thiourea (14) (0.50 g, 2.0 mmol) in 10 mL of anhydrous ethanol was refluxed under stirring for 20 h, and then cooled to room temperature. The solid was filtered. The crude white solid product was re-crystallized from methanol. The methanol solution was filtered while still hot to remove possible dust, and then heated into solution. It was re-crystallized two more times from methanol, and dried under vacuum to provide the desired product 19 as a white solid, yield 0.34 g (36%), HPLC purity 98.49%, mp >250° C. ¹HNMR (CD₃OD) δ 2.68 (s, 3H), 7.45 (s, 1H), 7.18 (s, 1H), 7.18-7.47 (m, 2H), 7.54-7.66 (m, 2H), 7.66 (d, 1H, J=4.4 Hz), 8.94 (d, 1H, J=4.4 Hz).

Synthesis of 2-(4-ethoxylphenyl)amino-4-(6-methylimidazo[2,1-b]thiazol-5-yl)-thiazole monohydrobromide (20)

A mixture of 2-bromo-1-(6-methylimidazo[2,1-b]thiazol-5-yl)ethanone hydrobromide (18) (2.20 g, 6.5 mmol) and (p-ethoxyphenyl)thiourea (10) (1.30 g, 6.5 mmol) in 40 mL of anhydrous ethanol was refluxed under stirring for 20 h, and then cooled to room temperature. The solid was filtered. The crude white solid product was re-crystallized from methanol. The methanol solution was filtered while still hot to remove possible dust, and then heated into solution. It was re-crystallized two more times from methanol, and dried under vacuum to provide the desired product 20 as a white solid, yield 0.64 g (22.4%), HPLC purity 97.81%, mp >240° C. ¹HNMR (CD₃OD) δ 1.27 (t, 3H, J=6.8 Hz), 2.56 (s, 3H), 3.88-3.94 (m, 2H), 6.85 (d, 2H, J=8.8 Hz), 6.97 (s, 1H), 7.34 (d, 2H, J=8.8 Hz), 7.54 (d, 1H, J=4.4 Hz), 8.44 (d, 1H, J=4.4 Hz). ESI-MS m/z 357 (M+1)⁺.

The representative derivatives listed in Tables 1 and 3-7 are readily synthesized utilizing similar procedures from known or readily available starting materials. The neutral compound was prepared as described above. Other salts were prepared as described above.

The alkyloxy and substituted alkyloxy derivatized compounds 25 and 26 are also synthesized according to the Schemes IV and V utilizing the parallel last combinatorial approach.

Scheme IV

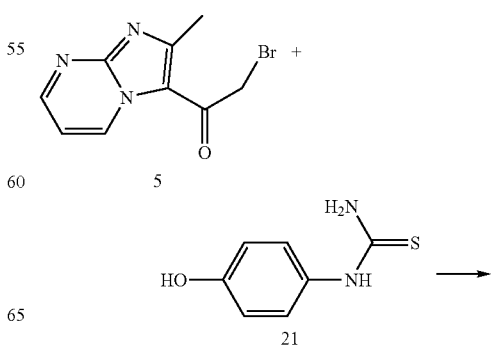

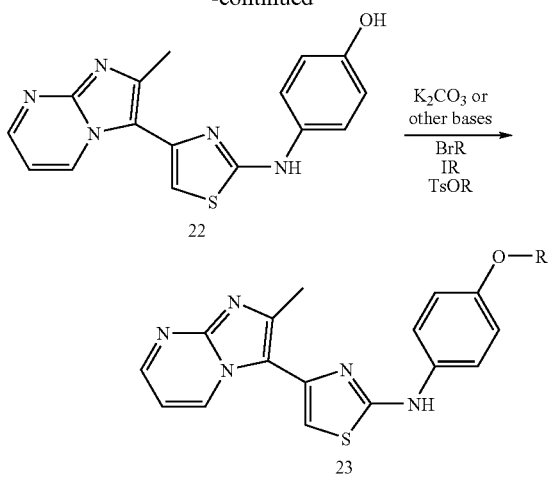

The intermediate bromide 5 is condensed with thiourea 21 utilizing the same procedure as the synthesis of 11 and 15 described above. The resulting compound 22 is reacted with reactive electrophiles, such as bromides, iodides, or tosylates, under basic conditions providing the desired products 23.

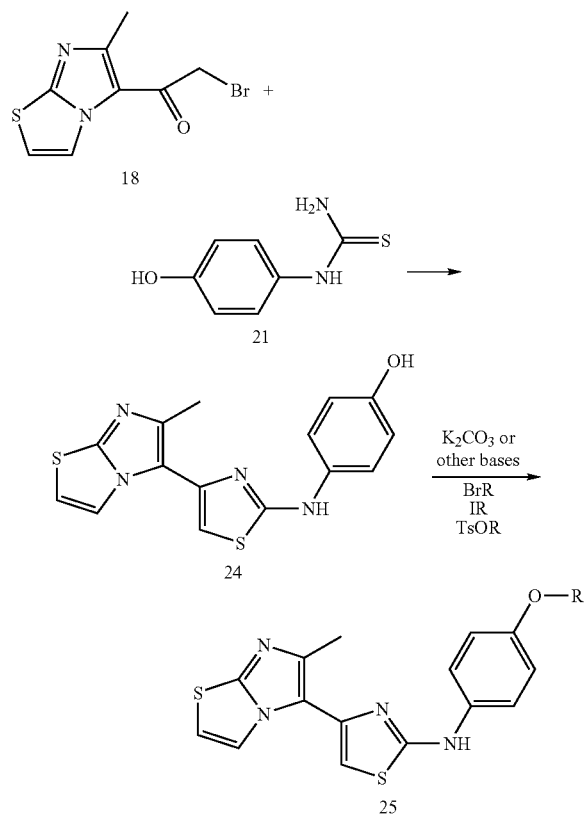

The intermediate bromide 18 is condensed with thiourea 21 utilizing the same procedure as the synthesis of 19 and 20 described above. The resulting compound 24 is reacted with reactive electrophiles, such as bromides, iodides, or tosylates, under basic conditions providing the desired products 25.

B.3. Formulation:

Any suitable formulation of the compounds described herein can be prepared. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by contacting a sufficiently basic compound such as an amine with a suitable acid, affording a physiologically acceptable salt. Alkali metal (e.g., sodium, potassium or lithium) or alkaline earth metal (e.g., calcium) salts of carboxylic acids also are included, and are prepared by conventional methods.

The invention also includes pharmaceutical compositions comprising at least one compound of the invention admixed with at least one pharmaceutically acceptable excipient. Preferably, at least one such excipient is an excipient other than water or a C1-C3 alcohol or a dimethyl sulfoxide.

Compounds of the invention can be administered by conventional routes, including orally, topically, transdermally, or by inhalation or injection. The compounds of the invention can be formulated by those skilled in the art by reference to known methods, and the formulation can be tailored according to the intended route of administration. Suitable methods for formulating organic compounds are described, for example, in REMINGTON'S PHARMACEUTICAL SCIENCES, 18$^{th}$ ed. (1990), which is incorporated herein by reference.

Where these compounds are administered in a pharmacological composition, it is contemplated that the compound can be formulated in admixture with a pharmaceutically acceptable carrier. For example, contemplated compounds can be administered orally as pharmacologically acceptable salts, or intravenously in a physiological saline solution. Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

The compounds having formula I-X as described herein are generally soluble in organic solvents such as chloroform, dichloromethane, ethyl acetate, ethanol, methanol, isopropanol, acetonitrile, glycerol, N,N-dimethylformamide, N,N-dimethylacetamide, dimethylsulfoxide, etc. In one embodiment, the present invention provides formulations prepared by mixing a compound having formula I-X with a pharmaceutically acceptable carrier. In one aspect, the formulation may be prepared using a method comprising: a) dissolving a described compound in a water-soluble organic solvent, a non-ionic solvent, a water-soluble lipid, a cyclodextrin, a vitamin such as tocopherol, a fatty acid, a fatty acid ester, a phospholipid, or a combination thereof, to provide a solution; and b) adding saline or a buffer containing 1-10% carbohydrate solution. In one example, the carbohydrate comprises dextrose. The pharmaceutical compositions obtained using the present methods are stable and useful for animal and clinical applications.

Illustrative examples of water soluble organic solvents for use in the present methods include and are not limited to polyethylene glycol (PEG), alcohols, acetonitrile, N-methyl-2-pyrrolidone, N,N-dimethylformamide, N,N-dimethylacetamide, dimethyl sulfoxide, or a combination thereof. Examples of suitable alcohols include but are not limited to methanol, ethanol, isopropanol, glycerol, or propylene glycol.

Illustrative examples of water soluble non-ionic surfactants for use in the present methods include and are not limited to CREMOPHOR® EL, polyethylene glycol modified CREMOPHOR® (polyoxyethyleneglyceroltriricinoleat 35), hydrogenated CREMOPHOR® RH40, hydrogenated CREMOPHOR®RH60, PEG-succinate, polysorbate 20, polysorbate 80, SOLUTOL® HS (polyethylene glycol 660 12-hydroxystearate), sorbitan monooleate, poloxamer, LABRAFIL® (ethoxylated persic oil), LABRASOL® (capryl-caproyl macrogol-8-glyceride), GELUCIRE® (glycerol ester), SOFTIGEN® (PEG 6 caprylic glyceride), glycerin, glycol-polysorbate, or a combination thereof.

Illustrative examples of water soluble lipids for use in the present methods include but are not limited to vegetable oils, triglycerides, plant oils, or a combination thereof. Examples of lipid oils include but are not limited to castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

Illustrative examples of fatty acids and fatty acid esters for use in the present methods include but are not limited to oleic acid, monoglycerides, diglycerides, a mono- or di-fatty acid ester of PEG, or a combination thereof.

Illustrative examples of cyclodextrins for use in the present methods include but are not limited to alpha-cyclodextrin, beta-cyclodextrin, hydroxypropyl-beta-cyclodextrin, or sulfobutyl ether-beta-cyclodextrin.

Illustrative examples of phospholipids for use in the present methods include but are not limited to soy phosphatidylcholine, or distearoyl phosphatidylglycerol, and hydrogenated forms thereof, or a combination thereof.

One of ordinary skill in the art may modify the formulations within the teachings of the specification to provide numerous formulations for a particular route of administration. In particular, the compounds may be modified to render them more soluble in water or other vehicle. It is also well within the ordinary skill of the art to modify the route of administration and dosage regimen of a particular compound in order to manage the pharmacokinetics of the present compounds for maximum beneficial effect in a patient.

C. Methods of Using the Invented Compounds and Pharmaceutical Compositions Thereof C.1. Methods of Using the Invented Compounds The compounds of the present invention can be used as cytotoxic and/or cytostatic agents in treating cancers or other types of proliferative disease. These compounds may function through any type of action mechanisms. For example, the compounds may inhibit molecules and/or signal transduction pathways leading to arrest of the cell cycle at G2/M phase, which might eventually induce apoptosis in tumor cells (see, e.g., Weung et al. (1997) *Biochim. Biophys. Res. Comm.*, vol: 263, pp 398-404). In another example, the compounds may disturb tubulin assembly/disassembly, which may inhibit the cell mitosis and induce the cell apoptosis (see, e.g., Panda et al., (1997) *Proc. Natl. Acad. Sci. USA*, vol: 94, 10560-10564). The compounds may also inhibit endothelial cell proliferation and angiogenesis effect (see, e.g., Witte et al., 1998, *Cancer Metastasis Rev.* vol. 17: 155-161).

In another aspect, the present invention is directed to a method of treatment of cancers of all tissue or organ origin including but not limited to sarcoma, epidermoid cancer, fibrosarcoma, cervical cancer, leukemia, lymphoma, lung cancer, non-small cell lung cancer, colon cancer, CNS cancer, melanoma, ovarian cancer, renal cancer, prostate cancer, breast cancer, head and neck cancers, pancreatic cancer and other types of proliferative disease in a mammal comprising administering a therapeutically effective amount of compound having Formula I-X as a cytotoxic and/or cytostatic agent to said subject in need of such treatment, in at least one treatment.

In yet another aspect, the present invention is directed to a method for manufacturing a pharmaceutical preparation for the treatment of cancers of all tissue or organ origin including but not limited to leukemia, lymphoma, lung cancer, colon cancer, CNS cancer, melanoma, ovarian cancer, renal cancer, prostate cancer or breast cancer, and other types of a proliferative disease, comprising admixing a therapeutically effective amount of a compound having Formula I-X with a pharmaceutically acceptable carrier.

To practice the method of the present invention, compounds having formula I-X and pharmaceutical compositions thereof may be administered orally, parenterally, by inhalation spray, topically, rectally, nasally, buccally, vaginally, via an implanted reservoir, or other drug administration methods. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. In some embodiments, the compounds of the invention are delivered by injection, i.e., parenterally. In some embodiments, the preferred route of administration is by intravenous or intraperitoneal injection.

A sterile injectable composition, such as a sterile injectable aqueous or oleaginous suspension, may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed include mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives, are useful in the preparation of injectables, as are pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Various emulsifying agents or bioavailability enhancers which are commonly used in the manufacture of pharmaceutically acceptable solid, liquid, or other dosage forms can also be used for the purpose of formulation.

A composition for oral administration may be any orally acceptable dosage form including, but not limited to, tablets, capsules, emulsions and aqueous suspensions, dispersions and solutions. In the case of tablets for oral use, commonly used carriers include lactose and corn starch. Lubricating agents, such as magnesium stearate, can also be added. For oral administration in a capsule form, useful diluents include lactose and dried corn starch. When aqueous suspensions or emulsions are administered orally, the active ingredient can be suspended or dissolved in an oily phase combined with emulsifying or suspending agents. If needed, certain sweetening, flavoring, or coloring agents can be added. A nasal aerosol or inhalation compositions can be prepared according to techniques well-known in the art of pharmaceutical formulation and can be prepared as solutions in, for example saline, employing suitable preservatives (for example, benzyl alcohol), absorption promoters to enhance bioavailability, and/or other solubilizing or dispersing agents known in the art.

An effective amount of a compound of the invention can be determined by routine experimentation as is known in the art. Typically, this involves administration of an amount shown to be well tolerated, and gradually increasing the dosage until a desired effect is achieved, such as reduction in symptoms, reduction n tumor size, or cessation of tumor growth. In some embodiments a starting dosage of about 5-10 mg/kg is used, and the dosage is increased incrementally once per week by about 50% each time until a desired effect is noted or tolerance problems are observed. In some embodiments, a suitable dosage is between about 5 and 250 mg/kg; or between about 10 and 150 mg/kg. Dosages between 10 and 100 mg/kg are sometimes preferred. Dosing can be done once, once weekly, once daily or more than once daily. In some embodiments, 1-4 doses are delivered per day to a subject in need of treatment.

In addition, the compounds having formula I-X may be administered alone or in combination with other anticancer agents for the treatment of various cancers or conditions. Combination therapies according to the present invention comprise the administration of at least one compound of the present invention or a functional derivative thereof and at least one other pharmaceutically active ingredient. The active ingredient(s) and pharmaceutically active agents may be administered separately or together. The amounts of the active ingredient(s) and pharmaceutically active agent(s) and the relative timings of administration will be selected in order to achieve the desired combined therapeutic effect.

In yet another aspect, the present invention is directed to a method of treatment of restenosis after coronary stenting for patients with coronary artery diseases with a compound having formula I-X.

The main cause of restenosis after coronary stenting for patients with coronary artery disease is neointimal hyperplasia resulting from the proliferation and migration of smooth-muscle cells and extracellular matrix productions (see, for example, "Pathology of acute and chronic coronary stenting in humans", by Farb, A., Sangiorgi, G., Certer, A. J., et al, in *Circulation*, vol. 99, pp 44-52, 1999). Compounds that have anti-proliferation capability may have an effect in reducing the risk of clinical and angiographic restenosis when such compounds are delivered with a suitable means (see, for example, "A polymer-based, paclitaxel-eluting stent in patients with coronary artery disease", by Stone, G. W., Ellis, S. G., Cox, D. A, et al, in *New England Journal of Medicine*, vol. 350: pp 221-231, 2004). Thus, with compounds having formula I-IX in treating tumor, they may be also useful in inhibiting proliferation of the cells involved in neointimal hyperplasia and thus reducing the incidence of neointimal hyperplasia and restenosis. Various methods may be used in delivering effectively the compounds to these cells. For example, a composition comprising above-described compounds having formula I-X can be administered orally, parenterally, or via an implanted reservoir. In other examples, the approaches described in the following papers may also be used: "A polymer-based, paclitaxel-eluting stent in patients with coronary artery disease", by Stone, G. W., Ellis, S. G., Cox, D. A. et al, in *New England Journal of Medicine*, vol. 350: pp 221-231, 2004; "A randomized comparison of a sirolimus-eluting stent with a standard stent for coronary revascularization", by Morice, M.-C., Serruys, P. W., Sousa, J. E., et al, in *New England Journal of Medicine*, vol. 346: pp 1773-1780, 2002; "Sirolimus-eluting stents versus standard stents in patients with stenosis in a native coronary artery", by Moses, J. W., Leon, M. B., Popma, J. J., et al, in *New England Journal of Medicine*, vol. 349: pp 1315-1323, 2003.

C.2. Biological Screening and Anticancer Activity:
C.2.1 In Vitro Cell-Based Screening Using Real-Time Cell Electronic Sensing (RT-CES) System The biological activity of compounds disclosed herein was monitored and profiled using the Real-Time Cell Electronic Sensing (RT-CES®) system from ACEA Biosciences, Inc. The RT-CES system utilizes cell-substrate impedance technology to monitor cellular behavior inside tissue culture wells in a microtiter plate format. The technology features in the integration of molecular and cell biology with microelectronics and is based on the electronic detection of biological assay process. The details of this cell electronic sensing technology and associated devices, systems and methods of use as described in U.S. provisional application No. 60/379,749, filed on Jul. 20, 2002; U.S. provisional application No. 60/435,400, filed on Dec. 20, 2002; U.S. Provisional application 60/469,572, filed on May 9, 2003, PCT application number PCT/US03/22557, filed on Jul. 18, 2003; PCT application number PCT/US03/22537, filed on Jul. 18, 2003; U.S. patent application Ser. No. 10/705,447, filed on Nov. 10, 2003; U.S. patent application Ser. No. 10/705,615, filed on Nov. 10, 2003, each of which is incorporated by reference. Additional details of RT-CES technology is further disclosed in U.S. provisional application No. 60/519,567, filed on Nov. 12, 2003, and U.S. provisional application No. 60/542,927, filed on Feb. 9, 2004.

For measurement of cell-substrate or cell-electrode impedance using RT-CES technology, microelectrodes having appropriate geometries are fabricated onto the bottom surfaces of microtiter plate or similar device, facing into the wells. Cells are introduced into the wells of the devices, and make contact to and attach to the electrode surfaces. The presence, absence or change of properties of cells affects the electronic and ionic passage on the electrode sensor surfaces. Measuring the impedance between or among electrodes provides important information about biological status of cells present on the sensors. When there are changes to the biological status of the cells analogue electronic readout signals are measured automatically and in real time, and are converted to digital signals for processing and for analysis. In a RT-CES system, a cell index (arbitrary representation of change in impedance) is automatically derived and provided based on measured electrode impedance values. The cell index obtained for a given well reflects: 1) how many cells are attached to the electrode surfaces in this well; 2) how well cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index.

The RT-CES system comprises three components, an electronic sensor analyzer, a device station and 16× or 96× microtiter devices. Microelectrode sensor array was fabricated on glass slides with lithographical microfabrication methods and the electrode-containing slides are assembled to plastic trays to form electrode-containing wells. The device station receives the 16× or 96× microtiter plate devices and is capable of electronically switching any one of the wells to the sensor analyzer for impedance measurement. In operation, the devices with cells cultured in the wells are placed into a device station that is located inside an incubator. Electrical cables connect the device station to the sensor analyzer. Under the RT-CES software control, the sensor analyzer can automatically select wells to be measured and continuously conduct impedance measurements. The impedance data from the analyzer is transferred to a computer, analyzed and processed by the integrated software.

Impedance measured between electrodes in an individual well depends on electrode geometry, ionic concentration in the well and whether there are cells attached to the electrodes. In the absence of the cells, electrode impedance is mainly determined by the ion environment both at the electrode/solution interface and in the bulk solution. In the presence of the cells, cells attached to the electrode sensor surfaces will alter the local ionic environment at the electrode/solution interface, leading to an increase in the impedance. The more cells there are on the electrodes, the larger the increase in cell-electrode impedance. Furthermore, the impedance change also depends on cell morphology and the extent to which cells attach to the electrodes.

To quantify cell status based on the measured cell-electrode impedance, a parameter termed Cell Index is derived. Cell Index is a quantitative measure of the status of the cells in an electrode-containing well. Under the same physiological conditions, more cells attached on to the electrodes leads to larger cell-electrode resistance value, leading to a larger value for Cell Index. Furthermore, for the same number of cells present in the well, a change in the cell status such as morphology will lead to a change in the Cell Index. For example, an increase in cell adhesion or cell spreading leads to larger cell-electrode contact area which will lead to an increase in cell-electrode resistance and thus a larger value for Cell Index.

Figure 1:
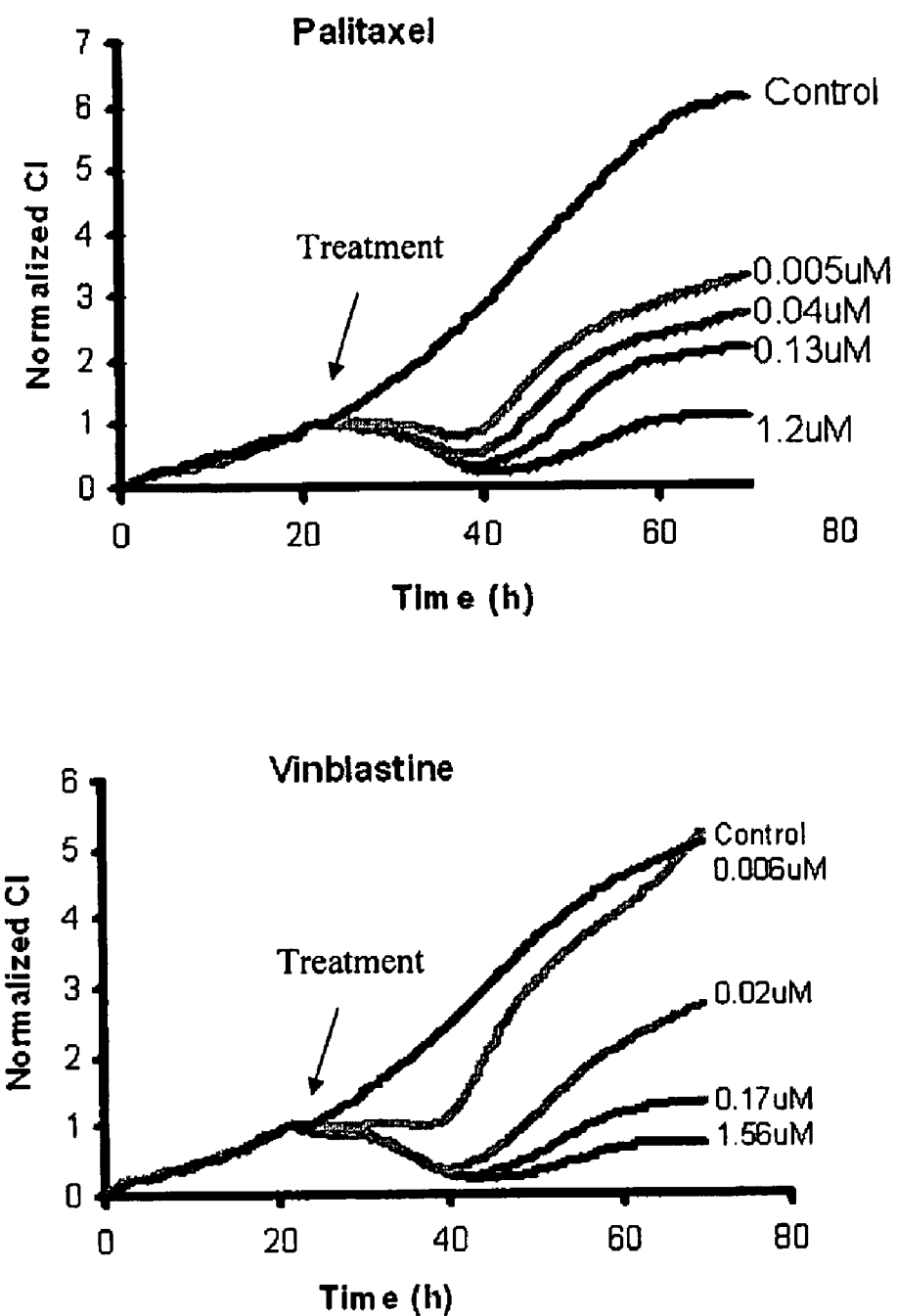
FIG. 1 shows the dynamic response pattern of A549 cells (human non small cell lung cancer cell line) to different concentrations of classical anti-mitotic agents paclitaxel and vinblastin, as determined on Real-Time Electronic Sensing System.

The interaction of biologically active compounds with cells growing inside the wells of the E-Plates results in unique activity patterns (i.e., unique cell impedance curves or cell index curves in response to a compound treatment) that is dependent on the biological mechanism of the compound itself, the concentration, length of incubation and the cell type. The "signature" cell responsive patterns to each compound correlates with specific biological phenomenon such as cell cycle arrest, morphology change and cell death. Cell response profiling on the RT-CES system has proven effective and we have shown that compounds with similar mechanism of action displays similar patterns. Thus, the similarity in the cell responsive patterns to compound treatment may indicate similarity in mechanism of action, mode of resistance and possibly molecular targets. We have identified a unique RT-CES signature pattern for cells undergoing mitotic arrest in response to treatment with anti-mitotic agents. As an example, FIG. 1 shows specific profile of A549 lung cancer cells treated with different concentrations of well know anti-mitotic agents paclitaxel and vinblastine. As shown by FIG. 1, the cell responsive patterns to paclitaxel and vinblastine compounds are very similar even though the potency may vary between the two compounds.

We have evaluated the response of a number of cancer cell lines to some of the invented compounds having formula I-X using RT-CES system. The time-dependent, cell responsive patterns of some of the invented compounds (at certain concentrations) were somewhat similar to those of paclitaxel and vinblastin (at certain concentrations). Thus, these compounds may have mechanisms of anticancer action similar to those of paclitaxel and vinblastin. On the other hand, these compounds may act on cancer cells through other mechanisms of action, different from those of paclitaxel and vinblastin, even though the time-dependent, cell responsive patterns of these invented compounds are similar to those of paclitaxel and vinblastin. It is also possible that these compounds act on cancer cells through multiple mechanisms of action, including the mechanism of action similar to those of paclitaxel and vinblastin.

Table 8 shows some representative compounds of the present invention whose in vitro and in vivo against tumor activities were studied. For the present invention, these compounds are numbered as No. 26, 2-(4-ethoxyphenyl)amino-4-(6-methylimidazo[1,2-a]pyrimidin-3-yl)thiazole (ACEA100160); No. 27, (2-(4-ethoxyphenyl)amino-4-(6-methylimidazo[2,1-b]thiazol-5-yl)thiazole (ACEA 100162); and No. 28, 2-(4-bromophenyl)amino-4-(6-methylimidazo[2,1-b]thiazol-5-yl)thiazole (ACEA100161).

TABLE 8

Structures of some exemplary compounds.

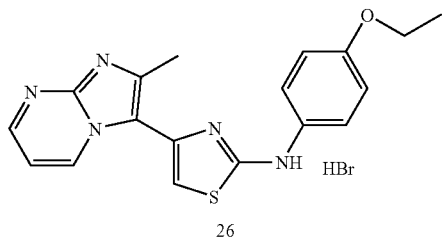

26

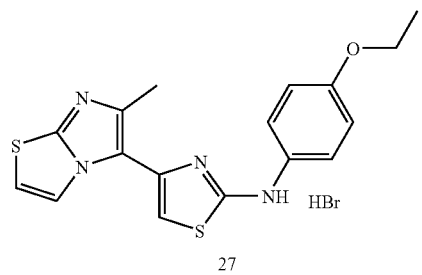

27

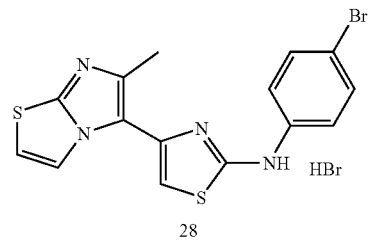

28

Compound 26 is 2-(4-ethoxyphenyl)amino-4-(6-methylimidazo[1,2-a]pyrimidin-3-yl)thiazole (ACEA100160). .
Compound 27 is 2-(4-ethoxyphenyl)amino-4-(6-methylimidazo[2,1-b]thiazol-5-yl)thiazole (ACEA100162).
Compound 28 is 2-(4-bromophenyl)amino-4-(6-methylimidazo[2,1-b]thiazol-5-yl)thiazole (ACEA100161).

Figure 2:
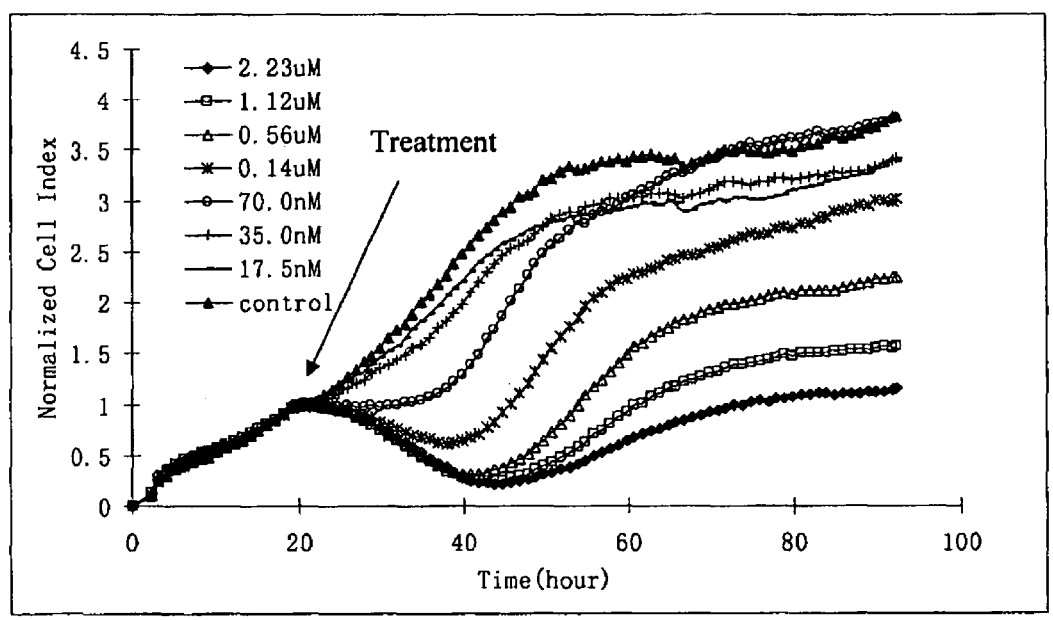
FIG. 2 shows the dynamic response pattern of A549 cells (human non small cell lung cancer cell line) to different concentrations of Compound No. 28 (2-(4-bromophenyl)amino-4-(6-methylimidazo[2,1-b]thiazol-5-yl)thiazole, ACEA100161) in Table 8, as determined on Real-Time Cell Electronic Sensing System.

In one example, FIG. 2 shows the time-dependent cell index for A549 cells prior to and after addition of different concentrations of compound No. 28 (2-(4-bromophenyl)amino-4-(6-methylimidazo[2,1-b]thiazol-5-yl)thiazole, or ACEA100161) in Table 8, as determined on Real-Time Cell Electronic Sensing System. As shown in FIG. 2, compound No. 28 (ACEA100161) exhibited inhibitory ability against the proliferation of A549 cells at various concentrations studied. Furthermore, the figure indicate that after compound addition (compound No. 28, or ACEA100161) at concentration of 0.14 uM or above, the cell indices for A549 cells first decreased with time and then increased, showing that A549 cells had complex kinetic responses to compound No. 28 (ACEA100161).

Figure 3:
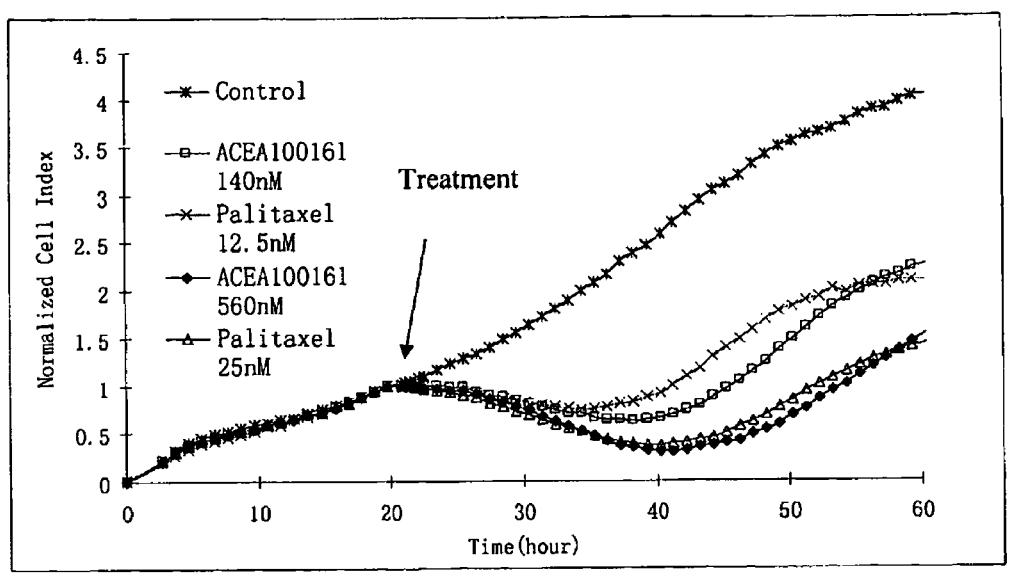
FIG. 3 shows the dynamic response pattern of A549 cell to different concentrations of paclitaxel and Compound 28 (ACEA100161) in Table 8, as determined on Real-Time Electronic Sensing System. Evidently, one can note that A549 cell exhibited similar responsive patterns to the compound No. 28 (ACEA100161) in Table 8 and to paclitaxel.

FIG. 3 shows the time-dependent cell index for A549 cells prior to and after addition of different concentrations of paclitaxel and compound No. 28 (ACEA00161) in Table 8, as determined on Real-Time Electronic Sensing System. Evidently, response pattern of A549 cells to 560 nM of compound No. 28 (ACEA100161) is somewhat similar to that of A549 cells to 25 nM of paclitaxel. Also, response pattern of A549 cells to 140 nM of compound No. 28 (ACEA100161) is somewhat similar to that of A549 cells to 12.5 nM of paclitaxel. Thus, the compound ACEA100161 may have mechanisms of anticancer action similar to those of paclitaxel. On the other hand, the compound ACEA100161 may act on cancer cells through other mechanisms of action, different from those of paclitaxel, even though the time-dependent, cell responsive patterns of compound ACEA100161 are similar to those of paclitaxel. It is also possible that the compound No. 28 (ACEA100161) act on cancer cells through multiple mechanisms of action, including the mechanism of action similar to those of paclitaxel.

Figure 4:
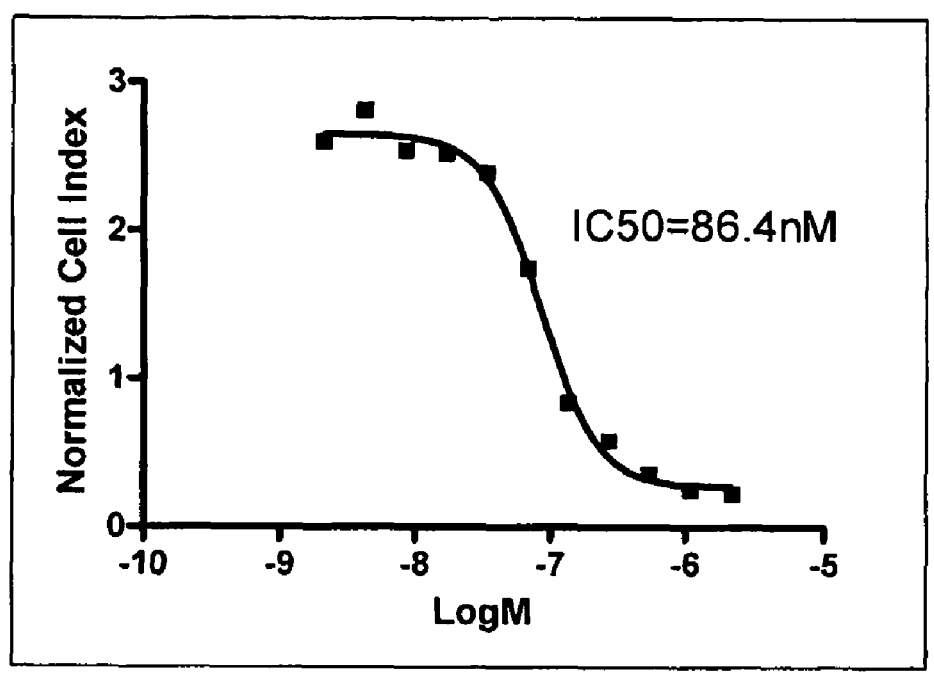
FIG. 4 shows dose response curves of A549 cells to the treatment of the compound No. 28 (2-(4-bromophenyl)amino-4-(6-methylimidazo[2,1-b]thiazol-5-yl)thiazole, ACEA100161) in Table 8, at the treatment time of 24 hrs after treatment.

FIG. 4 shows dose response curves of A549 cells to the treatment of the compound No. 28 (ACEA100161) in Table 8, at 24 hrs after treatment. The dose-response curve is obtained by plotting the normalized Cell Index value at 24 hours after compound treatment as a function of the compound concentration, based on dose-dependent response profiles shown FIG. 2. From the dose response curve in FIG. 4, one can calculate the IC50 values (i.e. the concentration of the compound at which cell proliferation has been inhibited by 50% due to compound treatment for a specified length of time) at 24 hours after compound treatment. The calculated $IC_{50}$ value for compound No. 28 (ACEA100161) is 86.4 nM.

Figure 5:
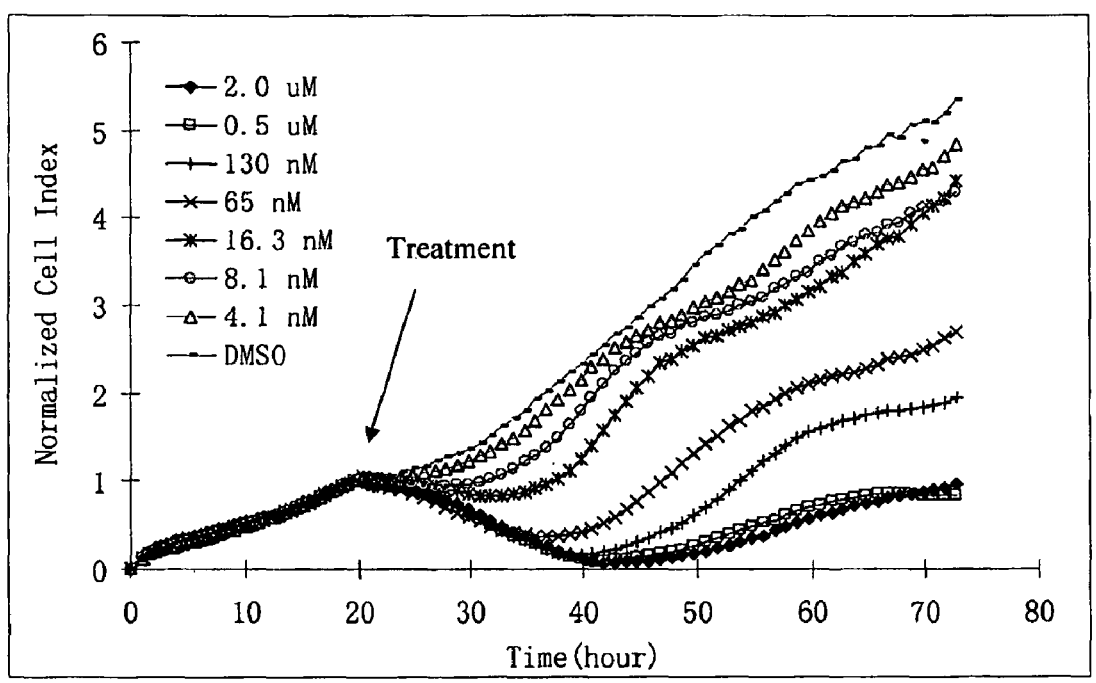
FIG. 5 shows the dynamic response pattern of A549 cells to different concentrations of compound No. 26 (2-(4-ethoxyphenyl)amino-4-(6-methylimidazo[1,2-a]pyrimidin-3-yl)

In another example, FIG. 5 shows the time-dependent cell index for A549 cells prior to and after addition of different concentrations of compound No. 26 (2-(4-ethoxyphenyl)amino-4-(6-methylimidazo[1,2-a]pyrimidin-3-yl)thiazole, ACEA100160) in Table 8, as determined on Real-Time Cell Electronic Sensing System. As shown in FIG. 5, ACEA100160 exhibited inhibitory ability against the proliferation of A549 cells at various concentrations studied. Furthermore, the figure indicate that after compound addition (ACEA100160) at concentration of 4.38 nM or above, the cell indices for A549 cells first decreased with time and then increased, showing that A549 cells had complex kinetic responses to ACEA100160.

FIG. 6 shows dose response curves of A549 cells to the treatment of the compound No. 26 (2-(4-ethoxyphenyl)amino-4-(6-methylimidazo[1,2-a]pyrimidin-3-yl)thiazole, ACEA100160) in Table 8, at 24 hrs after treatment. The dose-response curve is obtained by plotting the normalized Cell Index value at 24 hours after compound treatment as a function of the compound concentration, based on dose-dependent response profiles shown FIG. 5. From the dose response curve in FIG. 6, one can calculate the IC50 values (i.e. the concentration of the compound at which cell proliferation has been inhibited by 50% due to compound treatment for a specified length of time) at 24 hours after compound treatment. The calculated $IC_{50}$ value at 24 hr after treatment with ACEA100160 is 23.7 nM.

FIG. 7 shows the time-dependent cell index for A549 cells prior to and after addition of different concentrations of paclitaxel and compound No. 26 (2-(4-ethoxyphenyl)amino-4-(6-methylimidazo[1,2-a]pyrimidin-3-yl)thiazole, ACEA100160) in Table 8, as determined on Real-Time Electronic Sensing System. Evidently, response pattern of A549 cells to 35 nM of ACEA100160 is somewhat similar to that of A549 cells to 25 nM of paclitaxel. Also, response pattern of A549 cells to 140 nM of ACEA100160 is somewhat similar to that of A549 cells to 50 nM of paclitaxel. Thus, the compound ACEA100160 may have mechanisms of anticancer action similar to those of paclitaxel. On the other hand, ACEA100160 may act on cancer cells through other mechanisms of action, different from those of paclitaxel, even though the time-dependent, cell responsive patterns of ACEA100160 are similar to those of paclitaxel. It is also possible that ACEA100160 act on cancer cells through multiple mechanisms of action, including the mechanism of action similar to those of paclitaxel.

In yet another example, FIG. 8 shows the time-dependent cell index for A549 cells prior to and after addition of different concentrations of compound No. 27 (2-(4-ethoxyphenyl)amino-4-(6-methylimidazo[2,1-b]thiazol-5-yl)thiazole, ACEA100162) in Table 8, as determined on Real-Time Cell Electronic Sensing System. As shown in FIG. 8, ACEA100162 exhibited inhibitory ability against the proliferation of A549 cells at various concentrations studied. Furthermore, the figure indicate that after compound addition (ACEA100162) at concentration of 62.5 nM or above, the cell indices for A549 cells first decreased with time and then increased, showing that A549 cells had complex kinetic responses to ACEA100162.

FIG. 9 shows dose response curves of A549 cells to the treatment of the compound No. 27 (2-(4-ethoxyphenyl)amino-4-(6-methylimidazo[2,1-b]thiazol-5-yl)thiazole, ACEA100162) in Table 8, at 24 hrs after treatment. The dose-response curve is obtained by plotting the normalized Cell Index value at 24 hours after compound treatment as a function of the compound concentration, based on dose-dependent response profiles shown FIG. 8. From the dose response curve in FIG. 9, one can calculate the IC50 values (i.e. the concentration of the compound at which cell proliferation has been inhibited by 50% due to compound treatment for a specified length of time) at 24 hours after compound treatment. The calculated $IC_{50}$ value at 24 hr after treatment with ACEA100162 is 57.4 nM.

Different types of human cancer cells, including NCI-H460 (non-small cell lung cancer cells), MCF7 (breast cancer cells), SKOV3 (Ovarian cancer cells), Jurkat (Leukemia), PC3 (prostate cancer cells), Panc-1 (Pancreatic Carcinoma), SH-SY5Y (Neuroblastoma), HepG2 (human hepatosarcoma); GTL16 (Gastric carcinoma), B16-Iuc (Melanoma), KB (Head-Neck cancer cells), HeLa (Cervical carcinoma), HT1080 (fibrosarcoma cancer cells), MDCK (Kidney cells), HT29 (Colon cancer cells), A549 (non-small cell lung cancer cells) and other cell lines (see Table 9), with different numbers (2000 to 20,000 per well) were seeded into 16× or 96× microtiter E-Plate device and monitored by RT-CES™ system. The cells were allowed to grow for about 20 hours prior to the addition of compound 27 (2-(4-ethoxyphenyl)amino-4-(6-methylimidazo[2,1-b]thiazol-5-yl)thiazole, ACEA100162)) dissolved in DMSO solution (final DMSO concentration: 0.2%; final ACEA100162 concentration: between 3.13 nM and 200 nM). The cell-electrode impedance was continuously measured and the corresponding, time dependent, dose-dependent cell-index values were derived and recorded. Based on cell response profiles to different concentrations of compound ACEA100162, dose-response curves similar to those in FIG. 4 and FIG. 6 were plotted at selected time points of 24 hrs and 48 hrs after compound treatment. IC50 values were then calculated based on such dose response curves and are summarized in Table 9.

TABLE 9

IC50 values for compound 27 (2-(4-ethoxyphenyl)amino-4-(6-methylimidazo[2,1-b]thiazol-5-yl)thiazole, ACEA100162)) on various cell lines.

| Cell Source | Cell Line | IC50 (24 hr) | IC50 (48 hr) |
|---|---|---|---|
| Lung Cancer (Human) | H460 | 12.3 nM | 16 nM |
| Breast Cancer (Human) | MCF7 | >200 nM | >200 nM |
| Ovarian cancer (Human) | SKOV3 | 19.8 nM | 11.5 nM |
| Leukamia (Human) | Jurkat | 45.4 nM | N/A |
| Prostate Cancer (Human) | PC3 | 10.9 nM | 5.37 nM |
| Pancreatic Carcinoma (Human) | Panc-1 | 112.8 nM | 426.5 nM |
| Neuroblastmoa (Human) | SH-SY5Y | 13.4 nM | 6.7 nM |
| Hepatosarcoma (Human) | HepG2 | >200 nM | >200 nM |
| Gastric carcinoma (Human) | GTL16 | 138.5 nM | 2.1 nM |
| Melanoma (Rat) | B16-luc | 705.3 nM | 643.2 nM |
| Head-Neck (Human) | KB | 22.2 nM | 18.1 nM |
| Cervical carcinoma (Human) | Hela | 5.85 nM | 6.95 nM |
| Fibrosarcoma cancer (Human) | HT1080 | 2.39 nM | 2.69 nM |
| Kidney tumor (Monkey) | MDCK | 929.6 nM | 1.87 uM |
| Colon cancer (Human) | HT29 | 53.6 nM | 58.8 nM |
| fibroblast (Mouse) | 3T3 | 20.6 nM | 51.5 nM |
| Ovary adenocarcinoma (Human) | ST30 | 38.8 nM | 42.4 nM |
| Oral epitheliocarcinoma (Human) | KB200 | 12.1 nM | 4.28 nM |
| Breast adenocarcinoma (Human) | Bcap37 | 27.3 nM | 26 nM |
| Breast adenocarcinoma (Human) | MCF7adr | 12.3 nM | 12.5 nM |
| Gastric cancer (Human) | MKN45 | >200 nM | >200 nM |
| Lung carcinoma (Human) | A549 | 57.4 nM | 29.1 nM |

FIG. 10 shows the time-dependent cell index for a number of cell lines prior to and after addition of compound 27 (ACEA100162) at various concentrations. As shown in the Figures, ACEA100162 exhibited inhibitory effect on the proliferation of a number of cancer cell lines. The susceptibility to ACEA100162 differs among the cancer cell types. For some cancer cell types, a low dosage of ACEA100162 is sufficient to significantly inhibit cancer cell proliferation, whilst for other cancer cell types, a higher dosage is needed to achieve similar inhibition degree.

Different types of human cancer cells, including NCI-H460 (non-small cell lung cancer cells), MCF7 (breast cancer cells), SKOV3 (Ovarian cancer cells), Jurkat (Leukemia), PC3 (prostate cancer cells), Panc-1 (Pancreatic Carcinoma), SH-SY5Y (Neuroblastoma), HepG2 (human hepatosarcoma); GTL16 (Gastric carcinoma), B16-luc (Melanoma), KB (Head-Neck cancer cells), HeLa (Cervical carcinoma), HT1080 (fibrosarcoma cancer cells), MDCK (Kidney cells), HT29 (Colon cancer cells), A549 (non-small cell lung cancer cells) and other cell lines (see Table 10), with different numbers (2000 to 20,000 per well) were seeded into 16× or 96× microtiter E-Plate device and monitored by RT-CES™ system. The cells were allowed to grow for about 20 hours prior to the addition of (2-(4-ethoxyphenyl)amino-4-(6-methylimidazo[1,2-a]pyrimidin-3-yl)thiazole, ACEA100160) dissolved in DMSO solution (final DMSO concentration: 0.2%; final ACEA100160 concentration: between ~2.nM and ~2 uM. The cell-electrode impedance was continuously measured and the corresponding, time dependent, dose-dependent cell-index values were derived and recorded. Based on cell response profiles to different concentrations of compound ACEA100160, dose-response curves similar to those in FIG. 4 and FIG. 6 were plotted at selected time points of 24 hrs and 48 hrs after compound treatment. IC50 values were then calculated based on such dose response curves and are summarized in Table 10.

TABLE 10

IC50 values for compound 26 (2-(4-ethoxyphenyl)amino-4-(6-methylimidazo[1,2-a]pyrimidin-3-yl)thiazole, ACEA100160) on various cell lines.

| Cell Source | Cell Line | IC50 (24 hr) | IC50 (48 hr) |
|---|---|---|---|
| Lung Cancer (Human) | H460 | 30.7 nM | 34.0 nM |
| Breast Cancer (Human) | MCF7 | >1 uM | >1 uM |
| Ovarian cancer (Human) | SKOV3 | 104.5 nM | 82.1 nM |
| Leukamia (Human) | Jurkat | 27.2 nM | N/A |
| Prostate Cancer (Human) | PC3 | 10.6 nM | 78.9 nM (42 h) |
| Pancreatic Carcinoma (Human) | Panc-1 | 130.5 nM | 164.6 nM |
| Neuroblastmoa (Human) | SH-SY5Y | 49.7 nM | 41.4 nM (42 hr) |
| Hepatosarcoma (Human) | HepG2 | >2 uM | >2 uM |
| Gastric carcinoma (Human) | GTL16 | 147.6 nM | 0.4 nM |
| Melanoma (Rat) | B16-luc | 3.88 uM | 100 nM |
| Head-Neck (Human) | KB | 12.5 nM | 83.4 nM |
| Cervical carcinoma (Human) | Hela | 31.7 nM | 56.7 nM (42 hr) |
| Fibrosarcoma cancer (Human) | HT1080 | 17.7 nM | 25.5 nM |
| Kidney tumor (Monkey) | MDCK | 2.0 uM | 5.09 uM |
| Colon cancer (Human) | HT29 | 61.3 nM | 69.3 nM |
| Ovary adenocarcinoma (Human) | ST30 | 67.3 nM | 19.1 nM |
| Oral epithelioma (Human) | KB200 | 15.7 nM | 48.6 nM |
| Breast adenocarcinoma (Human) | Bcap37 | N/A | 87.1 nM |
| Breast adenocarcinoma (Human) | MCF7adr | 11.7 nM | 44.9 nM |
| Gastric cancer (Human) | MKN45 | 597.9 nM | 2.18 uM (42 hr) |
| Brain glioblastoma (Human) | A172 | 32.3 nM | 93.4 nM (42 h) |
| Desmoplastic cerebellar medulloblastoma (Human) | Daoy | 20.5 nM | 36.2 nM (42 hr) |
| Kidney transformed with adenovirus 5 DNA, (Human) | HEK-293 | 24.1 nM | 25.1 nM (42 hr) |
| Myoblast (Mouse) | C2C12 | 153.3 nM | 356.8 nM (42 hr) |
| Kidney SV40 transformed (Monkey) | COS1 | 120.7 nM | 304.5 nM (42 hr) |
| Lung carcinoma (Human) | A549 | 23.7 nM | 91.1 nM |

FIG. 11 shows the time-dependent cell index for a number of cell lines prior to and after addition of ACEA100160 at various concentrations. As shown in the FIG. 11, ACEA 100160 exhibited inhibitory effect on the proliferation of a number of cancer cell lines. The susceptibility to ACEA 100160 differs among the cancer cell types. For some cancer cell types, a low dosage of ACEA100160 is sufficient to significantly inhibit cancer cell proliferation, whilst for other cancer cell types, a higher dosage is needed to achieve similar inhibition degree.

EXAMPLE 1

Inhibition of Cell Proliferation by Compound No. 28 (2-(4-bromophenyl)amino-4-(6-methylimidazo[2,1-b]thiazol-5-yl)thiazole, ACEA100161) in A549 Cells The RT-CES System for such a study includes a RT-CES analyzer, an Mult-E-Plate Station, E-Plate device and RT-CES software. A549 cells (human lung cancer cells) were seeded at the density of 5000 cell in the wells of 96 well E-Plate devices. The E-Plates containing the cells were placed onto an Mult-E-Plate station inside the $CO_2$ incubator. The cell-electrode resistance for each well of the E-Plate devices is continuously monitored by RT-CES analyzer under the control of RT-CES software every 30 minutes. After about 20 hours, the measurement on RT-CES system was paused; the E-Plate was removed from the Mult-E-Plate station for compound addition. Compound ACEA100161 (or another compound being tested) which was dissolved in dimethyl-sulfoxide (DMSO) was serially diluted with 0.1% BSA in PBS and added to the wells containing the cell at a final concentration indicated in FIG. 2. Diluted DMSO solution served as solvent control and paclitaxel served as a positive control in the experiment. After compound addition, the E-Plates with added cells were reloaded back onto the Mult-E-Plate station for continuous measuring up to 72 hours. FIG. 2 shows the normalized cell index as a function of time prior to and after compound addition for different concentrations of Compound 28 (ACEA100161). The cell index data was normalized at the time point immediately prior to compound addition (about 20 hrs after cell seeding). In order to assess the potency of compound No. 28 (ACEA100161), we plotted the normalized cell-index values at a time point of 24 hrs after compound addition as a function of the compound concentration in FIG. 4, based on dose-dependent cell response profiles shown in FIG. 2. From the dose response curve in FIG. 4, one can calculate the IC50 values (i.e. the concentration of the compound at which cell proliferation has been inhibited by 50% due to compound treatment for a specified length of time) at 24 hours after compound treatment. The calculated $IC_{50}$ value for compound No. 28 (ACEA100161) is 86.4 nM.

EXAMPLE 2

Inhibition of Cell Proliferation by Compound 26 (2-(4-ethoxyphenyl)amino-4-(6-methylimidazo[1,2-a]pyrimidin-3-yl)thiazole, ACEA100160) in A549 Cells The RT-CES System for such a study includes a RT-CES analyzer, an Mult-E-Plate Station, E-Plate device and RT-CES software. A549 cells (human lung cancer cells) were seeded at the density of 5000 cell in the wells of 96 well E-Plate devices. The E-Plates containing the cells were placed onto an Mult-E-Plate station inside the $CO_2$ incubator. The cell-electrode resistance for each well of the E-Plate devices is continuously monitored by RT-CES analyzer under the control of RT-CES software every 30 minutes. After about 20 hours, the measurement on RT-CES system was paused; the E-Plate was removed from the Mult-E-Plate station for compound addition. Compound 26 (2-(4-ethoxyphenyl) amino-4-(6-methylimidazo[1,2-a]pyrimidin-3-yl)thiazole, ACEA100160) which was dissolved in dimethyl-sulfoxide (DMSO) was serially diluted with 0.1% BSA in PBS and added to the wells containing the cell at a final concentration indicated in FIG. 5. Diluted DMSO solution served as solvent control and paclitaxel served as a positive control in the experiment. After compound addition, the E-Plates with added cells were reloaded back onto the Mult-E-Plate station for continuous measuring up to 72 hours. FIG. 5 shows the normalized cell index as a function of time prior to and after compound addition for different concentrations of ACEA100160. The cell index data was normalized at the time point immediately prior to compound addition (about 20 hrs after cell seeding). In order to assess the potency of ACEA100160, we plotted the normalized cell-index values at a time point of 24 hrs after compound addition as a function of the compound concentration in FIG. 6, based on dose-dependent cell response profiles shown in FIG. 5. From the dose response curve in FIG. 6, one can calculate the IC50 values (i.e. the concentration of the compound at which cell proliferation has been inhibited by 50% due to compound treatment for a specified length of time) at 24 hours after compound treatment. The calculated $IC_{50}$ value for ACEA100160 is 23.7 nM.

EXAMPLE 3

Inhibition of Cell Proliferation by 27 (2-(4-ethoxyphenyl)amino-4-(6-methylimidazo[2,1-b]thiazol-5-yl)thiazole, ACEA100162) in A549 Cells The RT-CES System for such a study includes a RT-CES analyzer, a Mult-E-Plate Station, E-Plate device and RT-CES software. A549 cells (human lung cancer cells) were seeded at the density of 5000 cell in the wells of 96 well E-Plate devices. The E-Plates containing the cells were placed onto a Mult-E-Plate station inside the $CO_2$ incubator. The cell-electrode resistance for each well of the E-Plate devices is continuously monitored by RT-CES analyzer under the control of RT-CES software every 30 minutes. After about 20 hours, the measurement on RT-CES system was paused; the E-Plate was removed from the Mult-E-Plate station for compound addition. Compound 27 (2-(4-ethoxyphenyl)amino-4-(6-methylimidazo[2,1-b]thiazol-5-yl)thiazole, ACEA100162) which was dissolved in dimethyl-sulfoxide (DMSO) was serially diluted with 0.1% BSA in PBS and added to the wells containing the cell at a final concentration indicated in FIG. 8. Diluted DMSO solution served as solvent control and paclitaxel served as a positive control in the experiment. After compound addition, the E-Plates with added cells were reloaded back onto the Mult-E-Plate station for continuous measuring up to 72 hours. FIG. 8 shows the normalized cell index as a function of time prior to and after compound addition for different concentrations of ACEA100162. The cell index data was normalized at the time point immediately prior to compound addition (about 20 hrs after cell seeding). In order to assess the potency of ACEA100162, we plotted the normalized cell-index values at a time point of 24 hrs after compound addition as a function of the compound concentration in FIG. 9, based on dose-dependent cell response profiles shown in FIG. 8. From the dose response curve in FIG. 9, one can calculate the IC50 values (i.e. the concentration of the compound at which cell proliferation has been inhibited by 50% due to compound treatment for a specified length of time) at 24 hours after compound treatment. The calculated $IC_{50}$ value for ACEA100162 is 57.4 nM.

C.2.1 In Vivo Anticancer Efficacy

EXAMPLE 1

The Anti-Tumor Activity of ACEA100160 and ACEA100162 Against S180 Bearing Mouse Model A. Materials and Methods A.1 Compound and Solution ACEA100160 (2-(4-ethoxyphenyl)amino-4-(6-methylimidazo[1,2-a]pyrimidin-3-yl)thiazole) and ACEA 100162 (2-(4-ethoxyphenyl)amino-4-(6-methylimidazo[2,1-b]thiazol-5-yl)thiazole) are prepared at concentration of 8 mg/ml in solution containing 20% HP-beta-CD dextrose (D5W). The solvent HP-beta-CD solution is used as a vehicle negative control.

A.2 Animals

ICR mice, male, 21.4±1.5 g

A.3 Cell Lines

S180 sarcoma: murine cancer cell line S180.

The malignant ascites model of ICR mouse was induced by S180 cells.

A.4 Procedures

Under a sterilized condition, sacrifice the ICR murine S180 bearing mice, take out of the ascites and dilute with NS to certain cell numbers. Inject 0.2 ml cell suspension ($10^6$ cells) subcutaneously into the left flank on ICR mice. On the first treatment day before iv or ip, implanted animals are randomly divided into ten groups as following. The drugs were administrated in the schedule of Table 11 respectively. The solvent HP-beta-CD solution is used as a vehicle negative control. Observe clinical signs at least daily.

TABLE 11

Schedule of administration.

| Group # | # of Mice | Drug Route | Compound | Vol. (mL/10 g) | Dose (mg/kg) | Treatment Schedule | Diluent |
|---|---|---|---|---|---|---|---|
| 1 | 14 | IV | HP-beta-CD solution | 0.1 | — | qd, for 9 days | 1:1 |
| 2 | 6 | IP | ACEA100160 | 0.1 | 40 | qd, for 9 days | |
| 3 | 6 | IV | ACEA100160 | 0.1 | 40 | qd, for 9 days | 1:1 |
| 4 | 6 | IP | ACEA100162 | 0.1 | 40 | qd, for 9 days | |
| 5 | 6 | IP | ACEA100162 | 0.2 | 80 | qd, for 9 days | |
| 6 | 6 | IV | ACEA100162 | 0.1 | 40 | qd, for 9 days | |

A.5 Statistics

Tumor weight was recorded. The tumor inhibitory rate was calculated as follows: inhibitory rate=1−Wt/W0, where Wt is the average weight of each drug treatment group and W0 is the average weight of negative control group. Results are given as mean±SD values from n animals. Comparisons between groups were made with Student's two-tailed t test and a $P<0.05$ was considered significant.

B. Results

In murine S180 cancer bearing model, ACEA100160 40 mg/kg (qd, i,p) and 40 mg/kg (qd, i,v) groups inhibit S180 tumor growth, with the inhibitory rate value of 52.7% and 52.2% respectively. ACEA100162 40 mg/kg (qd, i,p), ACEA100162 80 mg/kg (qd, i,p) and ACEA100162 40 mg/kg (qd, i,v) groups showed anti-tumor activities with the inhibitory rate value of 59.3%, 77.2%, and 60.7% respectively.

EXAMPLE 2

The Anti-Tumor Activity of ACEA100160 and ACEA100162 Against LLC Mice Model

A. Materials and Methods

A.1 Compound and Solution

ACEA100160 (2-(4-ethoxyphenyl)amino-4-(6-methylimidazo[1,2-a]pyrimidin-3-yl)thiazole) and ACEA 100162 (2-(4-ethoxyphenyl)amino-4-(6-methylimidazo[2,1-b]thiazol-5-yl)thiazole) are prepared at concentration of 8 mg/ml in solution containing 20% HP-beta-CD dextrose (D5W). The solvent HP-beta-CD solution is used as a vehicle negative control.

A.2 Animals

C57 BL/6 mice, male, 19.1±1.0 g

A.3 Cell Lines

LLC: murine Lewis lung cancer cell line.

LLC cells were cultured in DMEM medium with 10% FBS to obtain the necessary cell number for injection subcutaneously ($10^7$ cells).

A.4 Procedures

Under a sterilized condition, sacrifice the C57 BL/6 murine LLC bearing mice, separate tumor and put it into NS. Chop the tumor into fine pieces with sterilized scissors and then homogenate into cell suspension. Inject 0.2 ml cell suspension ($10^6$ cells) subcutaneously into the left flank on C57 BL/6 mice. On the first treatment day before iv or ip, implanted animals are randomly divided into seven groups as following. The drugs were administrated in the schedule of Table 13 respectively. The solvent HP-beta-CD solution is used as a vehicle negative control. Observe clinical signs at least daily.

TABLE 12

Effects of ACEA100160 and ACEA100162 on ICR mice body weight and tumor weight at pre-dose and post-dose. ICR mice bearing S180 cancer were treated with ACEA100160 and ACEA100162 for 9 days ($\bar{x} \pm SD$).

| Groups | No. of Animals Start | No. of Animals End | Body Weight (g) Start | Body Weight (g) End | Tumor Weight (g) | Inhibition Rate (%) |
|---|---|---|---|---|---|---|
| Vehicle IP, qd | 14 | 12 | 21.7 ± 1.2 | 29.5 ± 2.8 | 1.49 ± 0.38 | — |
| 160 IP, 40 mg/kg | 6 | 6 | 21.5 ± 0.9 | 27.1 ± 2.2 | 0.70 ± 0.18** | 52.7 |
| 160 IV, 40 mg/kg | 6 | 5 | 21.6 ± 1.0 | 27.0 ± 3.7 | 0.71 ± 0.17** | 52.2 |
| 162 IP, 40 mg/kg | 6 | 5 | 20.6 ± 0.4 | 27.4 ± 1.5 | 0.61 ± 0.21** | 59.3 |
| 162 IP, 80 mg/kg | 6 | 6 | 21.8 ± 1.5 | 24.8 ± 2.0* | 0.34 ± 0.16** | 77.2 |
| 162 IV, 40 mg/kg | 6 | 6 | 21.0 ± 0.4 | 27.3 ± 1.2 | 0.59 ± 0.24** | 60.7 |

*$P < 0.05$;
**$P < 0.001$; VS control

TABLE 13

Schedule of Administration.

| Group # | # of Mice | Drug Route | Compound | Vol. (mL/10 g) | Dose (mg/kg) | Treatment Schedule | Diluent |
|---|---|---|---|---|---|---|---|
| 1 | 10 | IV | HP-beta-CD solution | 0.1 | — | qd, for 10 times | 1:1 |
| 3 | 6 | IP | ACEA100160 | 0.1 | 40 | qd, for 10 times | |
| 4 | 6 | IP | ACEA100162 | 0.1 | 40 | qd, for 10 times | 1:1 |
| 4 | 6 | IV | ACEA100162 | 0.1 | 40 | qd, for 10 times | |

A.5 Statistics

Tumor weight was recorded. The tumor inhibitory rate was calculated as follows: inhibitory rate=1-Wt/W0, where Wt is the average weight of each drug treatment group and W0 is the average weight of negative control group. Results are given as mean±SD values from n animals. Comparisons between groups were made with Student's two-tailed t test and a P<0.05 was considered significant.

B. Results

In murine Lewis lung cancer bearing model, ACEA100160 40 mg/kg (qd, i,p) group exhibited anti-tumor activities, with the inhibitory rate value of 27.13%, respectively. ACEA100162 40 mg/kg (qd, i,p) and ACEA100162 40 mg/kg (qd, i,v) groups showed anti-tumor activities, with the inhibitory rate value of 39.15%, and 25.5%, respectively (Table 14 and FIG. 13).

TABLE 14

Effects of ACEA100160 and ACEA100162 on C57 BL/6 mice body weight and tumor weight at pre-dose and post-dose. C57 BL/6 mice bearing LLC cancer were treated with ACEA100160, ACEA100162 and vehicle negative control for 12 days ($\bar{x} \pm SD$).

| Groups | No. of Animals Start | No. of Animals End | Body Weight (g) Start | Body Weight (g) End | Tumor Weight (g) | Inhibition Rate (%) |
|---|---|---|---|---|---|---|
| Vehicle IP, qod | 10 | 10 | 19.5 ± 1.1 | 21.1 ± 0.9 | 1.49 ± 0.30 | — |
| 160 IP, qod | 6 | 6 | 19.2 ± 0.9 | 21.2 ± 0.8 | 0.86 ± 0.37 | 27.1 |
| 162 IP, qod | 6 | 6 | 19.0 ± 0.8 | 21.1 ± 0.8 | 0.70 ± 0.46* | 39.2 |
| 162 IV, qod | 6 | 6 | 18.5 ± 1.3 | 21.1 ± 1.5 | 0.91 ± 0.18 | 25.5 |

*P < 0.05;
**P < 0.01; VS control

The invention claimed is:

1. A compound of formula IIIa:

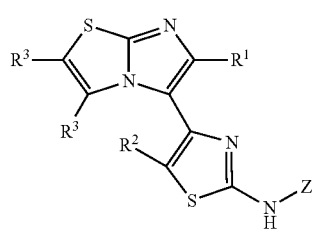

IIIa wherein $R^1$ is optionally substituted C1-C4 alkyl;

each $R^3$ is independently H, halo, C1-C4 alkoxy, or C1-C4 alkyl;

$R^2$ is H, halo, C1-C4 alkoxy, or C1-C4 alkyl;

wherein Z is selected from the group consisting of:

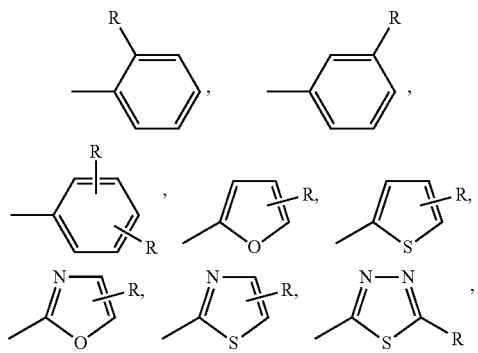

-continued

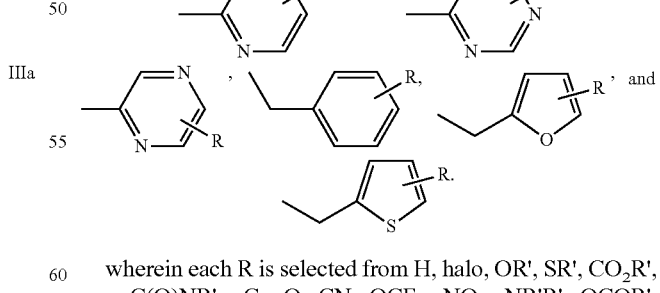

wherein each R is selected from H, halo, OR', SR', $CO_2R'$, $C(O)NR'_2$, C=O, CN, $OCF_3$, $NO_2$, NR'R', OCOR', $NR'SO_2R'$, $SO_2NR'R'$, $SO_3R'$, $P(O_3R')$, $CH(COOR')_2$, $CH(PO_3R')_2$, where R' is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, or R is $C_{1-8}$ alkyl, $C_{3-8}$ cyclic alkyl, $C_{2-8}$ alkenyl, $C_{2-8}$ alkynyl, an aryl, heteroaryl, a carbocyclic ring or a heterocyclic ring, each of which may contain a heteroatom;

or a pharmaceutically acceptable salt thereof.

2. A compound of formula IIIa:

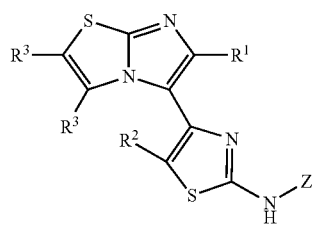

wherein $R^1$ is optionally substituted C1-C4 alkyl;

each $R^3$ is independently H, halo, C1-C4 alkoxy, or C1-C4 alkyl;

$R^2$ is H, halo, C1-C4 alkoxy, or C1-C4 alkyl;

wherein —NH—Z is selected from the group consisting of:

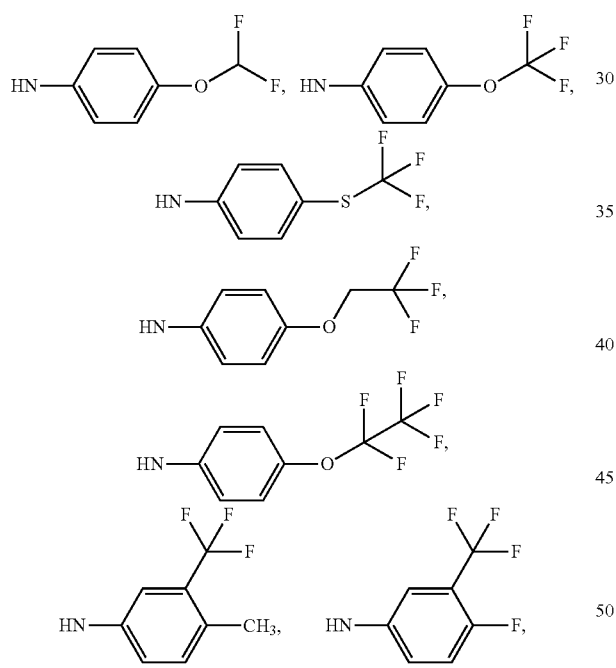

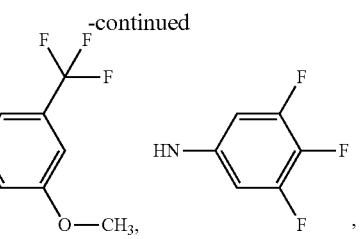

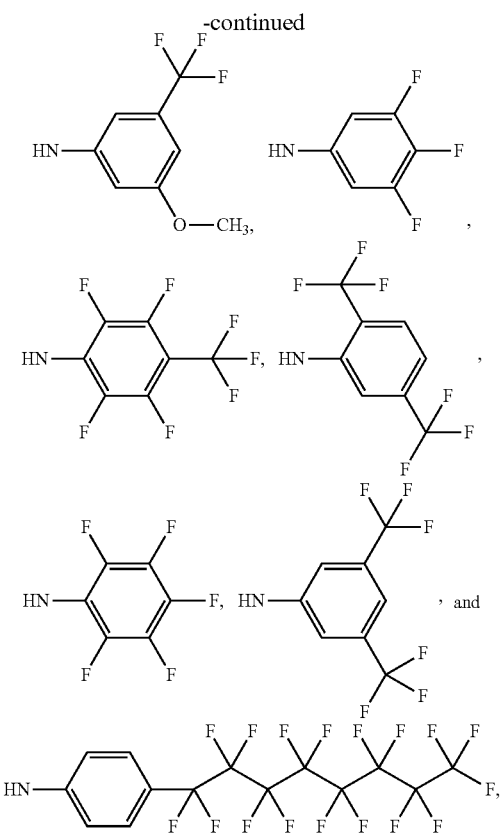

or a pharmaceutically acceptable salt thereof.

3. A compound of formula IIIa:

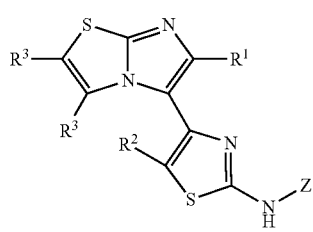

wherein $R^1$ is optionally substituted C1-C4 alkyl;

each $R^3$ is independently H, halo, C1-C4 alkoxy, or C1-C4 alkyl;

$R^2$ is H, halo, C1-C4 alkoxy, or C1-C4 alkyl;

wherein —NH—Z is selected from the group consisting of:

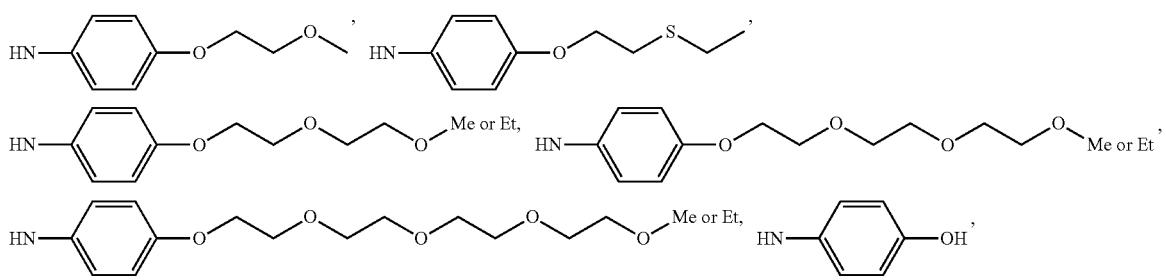

-continued

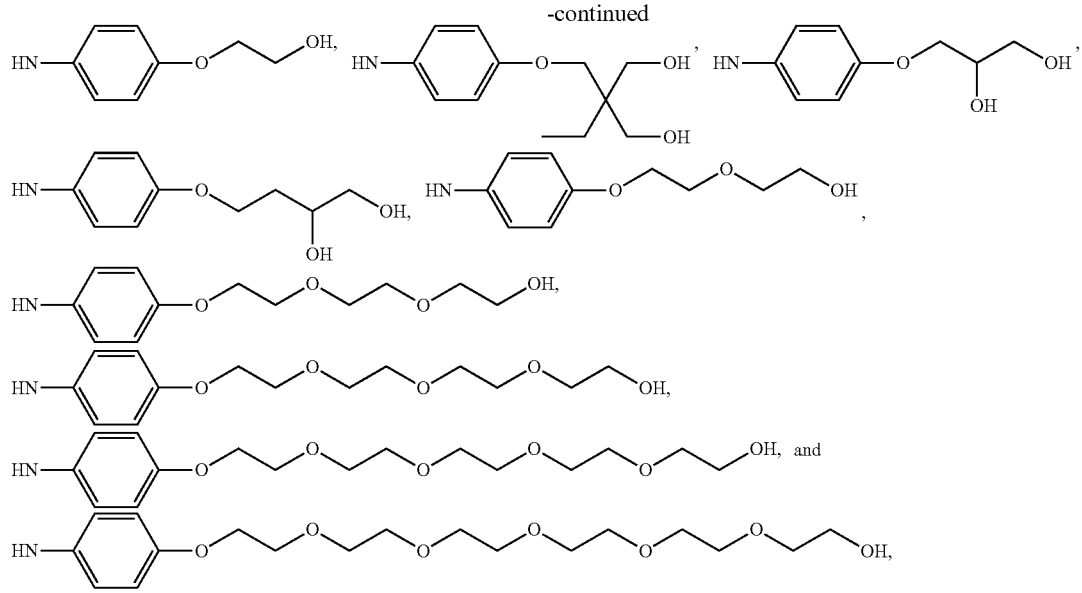

or a pharmaceutically acceptable salt thereof.

4. The compound of claim 1, wherein $R^1$ is methyl; or a pharmaceutically acceptable salt thereof.

5. The compound of claim 1, wherein $R^2$ is H; or a pharmaceutically acceptable salt thereof.

6. The compound of claim 1, wherein each $R^3$ is H; or a pharmaceutically acceptable salt thereof.

7. A pharmaceutical composition comprising a compound of claim 1, admixed with at least one pharmaceutically acceptable excipient.

8. A compound of claim 1, which compound is selected from the group consisting of:
   2-(4-ethoxyphenyl)amino-4-(6-methylimidazo[2,1-b]thiazol-5-yl)thiazole; and
   2-(4-bromophenyl)amino-4-(6-methylimidazo[2,1-b]thiazol-5-yl)thiazole;
or a pharmaceutically acceptable salt thereof.

9. A compound of formula IIIa:

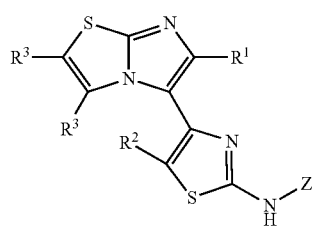

IIIa wherein $R^1$ is optionally substituted C1-C4 alkyl;

each $R^3$ is independently H, halo, C1-C4 alkoxy, or C1-C4 alkyl;

$R^2$ is H, halo, C1-C4 alkoxy, or C1-C4 alkyl;

wherein Z is:

wherein R is selected from H, halo, SR', $CO_2R'$, $C(O)NR'_2$, C=O, CN, $OCF_3$, $NO_2$, NR'R', OCOR', $NR'SO_2R'$, $SO_2NR'R'$, $SO_3R'$, $P(O_3R')$, $CH(COOR')_2$, $CH(PO_3R')_2$, where R' is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl;

or R is $C_{1-8}$ alkyl, $C_{3-8}$ cyclic alkyl, $C_{2-8}$ alkenyl, $C_{2-8}$ alkynyl, an aryl, heteroaryl, a carbocyclic ring or a heterocyclic ring, each of which may contain a heteroatom;

or a pharmaceutically acceptable salt thereof.

\* \* \* \* \*